United States Patent
Le Berre et al.

(10) Patent No.: US 9,024,061 B2
(45) Date of Patent: May 5, 2015

(54) METHANOL CARBONYLATION PROCESS WITH RHODIUM CATALYST AND A METALLIC CO-CATALYST SELECTED FROM TRANSITION METALS, ZINC, BERYLLIUM, INDIUM, TIN, STRONTIUM AND BARIUM

(75) Inventors: Carole M. Le Berre, Lacroix-Falgarde (FR); Samuel Gautron, Argelos (FR); Philippe J. Kalck, Auzeville-Tolosane (FR); Philippe G. Serp, Clermont le Fort (FR); Nicolas D. Lassauque, Nice (FR); G. Paull Torrence, League City, TX (US)

(73) Assignee: Celanese International Corporation, Irving, TX (US)

( * ) Notice: Subject to any disclaimer, the term of this patent is extended or adjusted under 35 U.S.C. 154(b) by 89 days.

(21) Appl. No.: 13/701,925

(22) PCT Filed: Jun. 14, 2010

(86) PCT No.: PCT/US2010/001698
§ 371 (c)(1),
(2), (4) Date: Feb. 20, 2013

(87) PCT Pub. No.: WO2011/159268
PCT Pub. Date: Dec. 22, 2011

(65) Prior Publication Data
US 2013/0165688 A1    Jun. 27, 2013

(51) Int. Cl.
*C07C 51/12*    (2006.01)
*C07C 51/47*    (2006.01)

(52) U.S. Cl.
CPC .................. *C07C 51/12* (2013.01); *C07C 51/47* (2013.01)

(58) Field of Classification Search
CPC .............................. C07C 51/12; C07C 51/44
See application file for complete search history.

(56) References Cited

U.S. PATENT DOCUMENTS

| | | | |
|---|---|---|---|
| 4,894,477 A | 1/1990 | Scates et al. | |
| 5,001,259 A | 3/1991 | Smith et al. | |
| 5,026,908 A | 6/1991 | Smith et al. | |
| 5,144,068 A | 9/1992 | Smith et al. | |
| 5,218,143 A | 6/1993 | Jones | |
| 5,416,237 A | 5/1995 | Aubigne et al. | |
| 5,663,430 A * | 9/1997 | Morris et al. | 562/608 |
| 5,939,585 A | 8/1999 | Ditzel et al. | |
| 6,137,000 A * | 10/2000 | Zoeller et al. | 560/207 |
| 6,303,813 B1 | 10/2001 | Scates et al. | |
| 6,323,364 B1 | 11/2001 | Agrawal et al. | |
| 6,657,078 B2 | 12/2003 | Scates et al. | |
| 7,053,241 B1 | 5/2006 | Torrence | |
| 7,276,626 B2 | 10/2007 | Gaemers et al. | |
| 7,368,597 B2 | 5/2008 | Gaemers et al. | |
| 2008/0071110 A1 | 3/2008 | Chen et al. | |

FOREIGN PATENT DOCUMENTS

| | | |
|---|---|---|
| CN | 1105603 | 7/1995 |
| CN | 1345631 | 4/2002 |
| CN | 1349855 | 5/2002 |
| CN | 1562937 A | 1/2005 |
| JP | 2005336105 | 12/2005 |
| WO | 2004101487 A1 | 11/2004 |
| WO | 2004101488 A1 | 11/2004 |
| WO | 2006064178 A1 | 6/2006 |

OTHER PUBLICATIONS

White et al, Basic Energy Sciences Advisory Committee Subpanel Workshop Report, Opportunities for Catalysis in the 21st Century, 2002, pp. 1-47.*
Ling et al, Hua Xue Tong Bao, Study of the effects of Rare Earth Metal Additives on Methanol Carbonylation Reaction, 2005, 68, pp. 1-6.*
Howard et al., Science and Technology in Catalysis 1999, "New Acetyls Technologies from BP Chemicals", pp. 61-68.
Ling et al., "Study of the Effects of Rare Earth Metal Additives on Methanol Carbonylation Reaction", Hua Xue Tong Bao [Notes of Chemistry], vol. 68, 2005.
Shao et al., "Study of the Effects of Metal Salts on Methanol Carbonylation Reaction", Journal of Molecular Catalysis (China), vol. 18, No. 6, Dec. 2004.
Watson, The Cativa™ Process for the Production of Acetic Acid, Chem. Ind. (Dekker) (1998) 75 Catalysis of Organic Reactions, pp. 369-380.
Pauling L., General Chemistry, "Titanium, Vanadium, Chromium, and Manganese and Their Congeners", Chapter 22 pp. 722-740 Dover (1988).
Kirk-Othmer Encyclopedia of Chemical Technology, "Rare-Earth Elements", Third Edition, vol. 19, pp. 833-854, John Wiley & Sons (1982).
Zhang et al., "Promoting effect of transition metal salts on rhodium catalyzed methanol carbonylation", Catalysis Communications 7 (2006), pp. 885-888.
Qian et al., "Promoting effect of oxometallic acids, heteropoly acids of Mo, W and their salts on rhodium catalyzed methanol carbonylation", Catalysis Communications 8 (2007), pp. 483-487.

* cited by examiner

*Primary Examiner* — Paul A Zucker
(74) *Attorney, Agent, or Firm* — Michael W. Ferrell; Ferrells, PLLC; Anna L. Kinney

(57) ABSTRACT

A carbonylation process for making acetic acid using a metallic co-catalyst composition, effective as a rhodium stabilizer and/or rate promoter, at molar ratios of metal/rhodium of about 0.5 to 40. The process includes reacting methanol with carbon monoxide in the presence of a rhodium-based catalytic metal complex with about 1 to 20 weight percent methyl iodide, less than about 8 weight % water and about 0.5 to about 30 weight percent methyl acetate. The crude acetic acid is flashed and further purified.

15 Claims, 5 Drawing Sheets

IMPURITIES AS A FUNCTION OF IODIDE FOR Rh/METALS

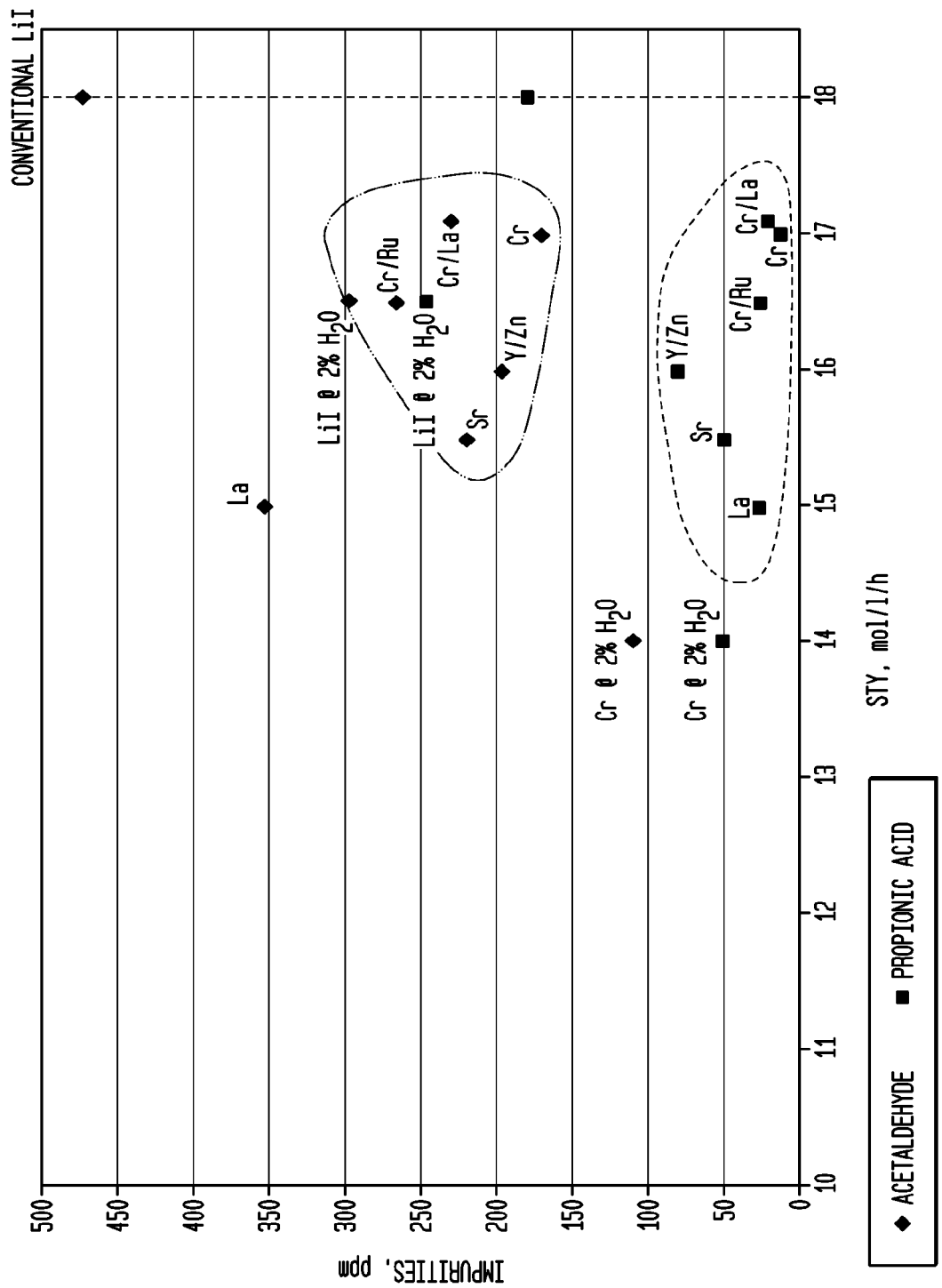

METHANOL CARBONYLATION PROCESS WITH RHODIUM CATALYST AND A METALLIC CO-CATALYST SELECTED FROM TRANSITION METALS, ZINC, BERYLLIUM, INDIUM, TIN, STRONTIUM AND BARIUM

CLAIM FOR PRIORITY

This application is a national phase entry of International Application No. PCT/US2010/001698, filed Jun. 14, 2010, entitled "Carbonylation Process". The priority of International Application No. PCT/US2010/001698 (PUBLISHED AS WO 2011/159268) is hereby claimed and its disclosure incorporated herein by reference in its entirety.

TECHNICAL FIELD

The present invention relates to methanol carbonylation to make acetic acid using an aqueous homogeneous rhodium catalyst medium with one or more stabilizing and promoting metals selected and utilized under conditions which generate substantially less than a theoretically equivalent amount of inorganic iodide corresponding to the concentration of metal added. Metal/rhodium molar ratios of from about 0.5:1 to about 30:1 are employed. The process is carried out under low water conditions, suitably from about 0.1-10 wt % water in the reactor. Suitable stabilizing and promoting metals are, for example, strontium; nickel; tin; chromium; lanthanum; or a combination of yttrium, vanadium, or barium with zinc, ruthenium, tin, manganese or a heteropoly acid.

BACKGROUND

Reaction systems of choice to manufacture acetic acid in high yields, on a large scale with economically viable production rates, include those with a relatively low water (less than 14 wt %) aqueous rhodium catalyst system which includes an iodide salt. See, for example, U.S. Pat. No. 5,144,068 to Smith et al. and U.S. Pat. No. 6,657,078 to Scates et al. So called "low water" processes for making acetic acid have much better carbon monoxide efficiency than conventional Monsanto processes due, in part, to less generation of hydrogen and carbon dioxide by way of the water gas shift reaction.

Commercial systems typically have corrosion metals present in the catalytic medium which result in relatively low levels of iodide salts in the presence of methyl iodide under reaction conditions. In general, conventional wisdom is that corrosion metals (i.e., iron, nickel, chromium, molybdenum, and the like) are not as effective as alkali metals such as lithium in providing inorganic iodide to the system and thereby stabilizing the rhodium catalyst (a significant cost of production) under reduced carbon monoxide pressure as is encountered in a flash vessel. Moreover, corrosion metals have been considered undesirable due to solubility and by-product issues. See U.S. Pat. No. 4,894,477 to Scates et al., Col. 2, line 13 and following, as well as Col. 9, Table 1. As one of skill in the art will be aware, iodide salt containing systems are highly effective as to stabilizing the rhodium from precipitating under reduced carbon monoxide partial pressures as well as maintaining production rates under low water conditions. The rhodium/lithium iodide system has drawbacks, however, notably: (1) the reaction medium is highly corrosive due, in part, to the elevated levels of iodide salt and (2) the rhodium/lithium iodide system tends to generate a plethora of aldehyde-related impurities such as propionic acid, acetaldehyde, crotonaldehyde, higher unsaturated aldehydes, and higher alkyl iodides, all of which are difficult to remove. See Howard et al., Science and Technology in Catalysis 1998, p 64-65 and D. J. Watson, Proceedings of the 17th ORCS Meeting, Marcel Dekker (1998) for more information relating to corrosion and impurities.

Ruthenium and other metals have been considered for their ability to promote higher production rates in combination with iodide salts. Chinese Patent No. 1,562,937 to Haojing Chemical Co., Ltd., discloses use of ruthenium as a co-catalyst at a molar ratio to rhodium of 2.9:1, with a water concentration of 3 to 14.5 wt % and a 15.5 wt % iodide concentration at a rhodium concentration of 1000 ppm (see Table 1). U.S. Pat. No. 5,939,585 to Ditzel et al. disclose use of ruthenium or osmium as a promoter (Claim 1) at a molar ratio to rhodium range of 0.1:1 to 20:1 (Col. 3, lines 58-59) and a water concentration of 0.1 to 7 wt %. U.S. Pat. Nos. 7,368,597 and 7,276,626 both to Gaemers et al. (equivalent to WO 2004/101487 and WO/2004/101488, respectively) show the use of osmium, rhenium, cadmium, mercury, tungsten, ruthenium or zinc as a rate promoter (¶0059) at a molar ratio to rhodium of 0.1:1 to 20:1 (¶0069) with a water concentration of 0.1 to 30 wt % (¶0081). Gaemers et al. also disclose the use of iodide complexes of lanthanide metals, molybdenum, nickel, iron and chromium as stabilizers (¶0070). However, Gaemers et al. primarily rely on a ligand to impart catalyst stability.

Other references likewise disclose the use of additional metals in a rhodium/iodide catalyst system for making acetic acid. U.S. Pat. No. 7,053,241 to Torrence discloses the use of tin or ruthenium in a range of molar ratios to rhodium of 0.1:1 to 20:1 (Abstract) at a water concentration of 0.1 to 14 weight % (Col. 4, lines 7-15). The process disclosed in Torrence '241 includes the presence of an iodide ion concentration greater than about 3 wt % as does most of the literature discussing metal promoters/stabilizers in a methanol carbonylation process at water concentrations of less than 14% by weight. United States Publication No. 2008/0071110 to Chen et al., now U.S. Pat. No. 7,671,233, for example, show use of lanthanides, copper, titanium, zirconium, vanadium, manganese, cobalt, palladium, tin, chromium, nickel, molybdenum, or zinc (¶0014) as a promoter in a range of molar ratios to rhodium of about 0.1:1 to about 7:1 (¶0016 and Examples) at a water concentration of 1 to 14 weight %. Chen et al. also discuss the use of yttrium in a molar ratio to rhodium range of 0.09:1 to 5:1 without another stabilizing component; however, in virtually all cases, significant iodide levels are reported and the apparent intended function of the metal promoter/stabilizer is to stabilize inorganic iodide concentration which, in turn, stabilizes the catalyst solution.

Japanese Kokai Patent Application 2005-336105 to Daicel Chemical Industries Ltd., now Japanese Patent No. JP 4657632 B2, discloses a method for manufacturing carboxylic acid in the presence of a rhodium catalyst, lithium iodide at a concentration of 0.1 to 30 wt %, a limited amount of water (15 wt % or less), and at least one element or element-containing compound selected from Zn (in a concentration of 10-5,000 ppm), Sn, Ge, and Pb (in concentrations of 10-20,000 ppm). U.S. Pat. No. 5,218,143 to Jones shows rhodium catalyzed carbonylation with 0.5 to 5 wt % water stabilized with lithium iodide (2-20 wt %; approximately 120:1 to 1200:1 Li:Rh molar ratio) and a Group VI B metal costabilizer, i.e., chromium, molybdenum, or tungsten, in a concentration of 0-10,000 ppm which corresponds to a metal:Rh molar ratio of approximately 0:1 to 276,000:1. The lithium iodide concentrations of Jones are significantly higher than those of the present invention.

Still other metal iodides have been considered as alternative stabilizers to lithium iodide. For instance, U.S. Pat. No.

5,416,237 to Aubigne et al. discloses use of beryllium iodide as a stabilizer, (Col. 3, lines 43-49) using up to 10 weight % water.

Various alternatives to rhodium/lithium iodide systems have been suggested based on laboratory batch unit data, typically including relatively low levels of metal salts, generally at equimolar amounts with rhodium or less. In this regard, see Zhang et al., "Promoting effect of transition metal salts on rhodium catalyzed methanol carbonylation", Catalysis Communications 7 (2006), pp. 885-888; Ling et al., "Study of the Effects of Rare Earth Metal Additives on Methanol Carbonylation Reaction", Hua Xue Tong Bao [Notes of Chemistry], Vol. 68, 2005; and Shao et al., "Study of the Effects of Metal Salts on Methanol Carbonylation Reaction", Journal of Molecular Catalysis (China), Vol. 18, No. 6, December, 2004. So also, it has been suggested to use heteropoly acids of molybdenum and tungsten with rhodium catalysts to make acetic acid, also at relatively low metal concentrations. See Qian et al., "Promoting effect of oxometallic acids, heteropoly acids of Mo, W and their salts on rhodium catalyzed methanol carbonylation", Catalysis Communications 8 (2007), pp. 483-487. All four documents provide experimental data derived from a batch process, with results determined as soon as 5 minutes into the reaction. These data do not predict results in a continuous process at equilibrium, nor does the data supply information concerning the stability of the catalyst system at reduced carbon monoxide pressure as is seen in a flash vessel of a production unit. With respect to Zhang et al., it is noted that, although metal:rhodium molar ratios (Cr, Fe, Ni, and Zn) of from 2.4 to 4.7 were considered (Table 1), the rate data were determined after 5 minutes. Similarly, with regard to Ling et al., the reaction times were no higher than 55 minutes (Table 1), and only consider a single promoter molar ratio of 1:1 (Nd, Ce, or La:Rh). Furthermore, Shao et al. again provided data after only 10 minutes of reaction time (FIG. 1) for metal:rhodium (Sn, Pb, Cr, and Zr) molar ratios of 0.5:1 to 2.5:1. Note that the tin promoter used was $SnCl_2$. Finally, Qian et al. provided data collected after 5 minutes of reaction time (page 484) for HPA:rhodium molar ratios of from 0.2:1 for phosphotungstic acid (PTA) and sodium phosphotungstate (SPT) to 6:1 for $Na_2MoO_4$. In any event, the various papers referred to in this paragraph appear to be directed to identifying metals or metal-containing compositions which provide a substantial iodide concentration to stabilize the rhodium catalyst.

WIPO Publication WO 2006/064178 to BP Chemicals Limited teaches a catalyst system for the production of acetic acid which comprises a rhodium carbonylation catalyst, methyl iodide, and at least one non-hydrohalogenoic acid promoter, such as a heteropoly acid, in the presence or absence of alkali metal iodides, alkaline earth iodides or other components, such as amines or phosphine derivatives, recognized as capable of generating $I^-$ by reaction with alkyl iodides such as methyl iodides. The WO '178 publication teaches to optionally include a copromoter capable of generating ionic iodide such as lithium iodide, lanthanide metals, nickel, iron, aluminum, and chromium. It is seen in the Examples which follow that chromium, for example, may be used in accordance with the present invention without forming inorganic iodide at or near theoretically equivalent amounts corresponding to the concentration of chromium added, contrary to the teachings of the WO '178 publication.

As the methanol carbonylation process has been practiced at increasingly lower water concentrations other problems have been found to have arisen. Specifically, operating at this new lower water regime has exacerbated certain impurities in the product acetic acid. As a result, the acetic acid product formed by the above-described low water carbonylation is frequently deficient with respect to the permanganate time owing to the presence therein of small proportions of residual impurities. Since a sufficient permanganate time is an important commercial test which the acid product must meet for many uses, the presence therein of such impurities that decrease permanganate time is objectionable [Ullman's Encyclopedia of Industrial Chemistry, "Acetic Acid", Volume A1, p. 56, $5^{th}$ ed]. Of particular concern are certain carbonyl compounds and unsaturated carbonyl compounds, particularly acetaldehyde and its derivatives, crotonaldehyde and 2-ethyl crotonaldehyde (also referred to as unsaturated aldehyde impurities). However, other carbonyl compounds known also to affect the permanganate time are acetone, methyl ethyl ketone, butyraldehyde, and 2-ethyl butyraldehyde. Thus, these carbonyl impurities affect the commercial quality and acceptability of the product acetic acid. If the concentration of carbonyl impurities reaches only 10-15 ppm, the commercial value of the product acetic acid will certainly be negatively affected. As used herein the phrase "carbonyl" is intended to mean compounds which contain aldehyde or ketone functional groups which compounds may or may not possess unsaturation.

It is postulated in an article by Watson, The Cativa™ Process for the Production of Acetic Acid, Chem. Ind. (Dekker) (1998) 75 Catalysis of Organic Reactions, pp. 369-380, that enhanced rhodium catalyzed systems have increased standing levels of rhodium-acyl species which will form free acetaldehyde at a higher rate. The higher rate of acetaldehyde formation can lead to the increased production of permanganate reducing compounds.

The precise chemical pathway within the methanol carbonylation process that leads to the production of crotonaldehyde, 2-ethyl crotonaldehyde and other permanganate reducing compounds is not well understood. One prominent theory for the formation of the crotonaldehyde and 2-ethyl crotonaldehyde impurities in the methanol carbonylation process is that they result from aldol and cross-aldol condensation reactions starting with acetaldehyde. Because theoretically these impurities begin with acetaldehyde, many previously proposed methods of controlling carbonyl impurities have been directed towards removing acetaldehyde and acetaldehyde-derived carbonyl impurities from the reaction system. So also, operation at reduced hydrogen partial pressure and/or reduced methyl iodide has been proposed. See U.S. Pat. No. 6,323,364 to Agrawal, et al., as well as U.S. Pat. No. 6,303,813 to Scates et al., the disclosures of which are incorporated herein by reference.

Conventional techniques used to remove acetaldehyde and carbonyl impurities have included treatment of acetic acid with oxidizers, ozone, water, methanol, amines, and the like. In addition, each of these techniques may or may not be combined with the distillation of the acetic acid. The most typical purification treatment involves a series of distillations of the product acetic acid. Likewise, it is known to remove carbonyl impurities from organic streams by treating the organic streams with an amine compound such as hydroxylamine which reacts with the carbonyl compounds to form oximes followed by distillation to separate the purified organic product from the oxime reaction products. However, this method of treating the product acetic acid adds significant cost to the process.

Despite much effort and substantial need in the art for an improved low water, rhodium catalyzed methanol carbonylation process without elevated levels of inorganic iodide, little progress has been made and the rhodium/lithium iodide system remains the system of choice for commercial production because of the rhodium stability provided under reduced carbon monoxide pressure as is seen in the flasher of a continuous production unit.

SUMMARY OF INVENTION

We have unexpectedly found that by judicious choice of a transition metal (or selected other metal) co-catalyst composition effective as a stabilizer and promoter and utilizing the metals in specified molar ratios with rhodium, that a low water acetic acid process can be operated with inorganic iodide concentrations that are substantially lower than the theoretically equivalent amount correspondent to the concentration of the added metals, while preserving catalyst stability and achieving high rates. The results are surprising in view of conventional wisdom in the art that a substantial inorganic iodide content must be provided under low water conditions in order to prevent precipitation of rhodium in the form of rhodium triiodide because of low levels of hydriodic acid (HI) in equilibrium with methyl iodide at low water levels. Iodide salts are also rate promoters which make conventional systems employing them economically attractive. Further, one of skill in the art would have expected inorganic iodide concentrations in the reaction mixture due to addition of stabilizer and promoter metals to be substantially equivalent with the metals present; e.g., that approximately three moles of inorganic iodide would be present for every mole of trivalent metal added.

Particularly surprising features of the present invention include that certain metals and combinations thereof provide both (1) rhodium stability under low water conditions especially where reduced carbon monoxide partial pressure is encountered and (2) elevated acetic acid production rates under low water conditions, without maintaining elevated levels of inorganic iodide in the system. The rate promoting and stabilizing compositions may even be added as metal iodides if so desired; there may be little substantial additional inorganic iodide in the system due to the addition of such compounds. It is believed that the iodide added in such cases is primarily consumed in the system by equilibria, producing methyl iodide and resulting in higher levels of metal acetates which provide catalyst stability and promote production rates.

The benefits of the invention are at least three-fold. First, the low inorganic iodide levels make the catalyst system less corrosive than conventional low water catalyst systems, reducing or eliminating corrosion problems. Metallurgy requirements for equipment are also less stringent. Thus, capital and operating costs are reduced. Second, many of the impurity issues arising from elevated levels of inorganic iodide in the system may be ameliorated or overcome. Without intending to be bound by theory, it is believed that many of the impurities are derived from acetaldehyde, as noted above, which appears to form more readily in the presence of iodide salts, for example lithium iodide. Acetaldehyde is believed to condense to form unsaturated aldehydes, such as crotonaldehyde, which then generate higher alkyl iodides in the system which are particularly difficult to remove. So also, acetaldehyde formation appears to cause increases in propionic acid levels because of the availability of hydrogen in the reactor. As inorganic iodide levels are lowered in accordance with the invention, acetaldehyde and related impurities are reduced.

A third benefit arises from the increased production rates at low water conditions. Without intending to be bound by theory, the metallic co-catalyst composition in the presence of very low inorganic iodide accelerates the reductive elimination step of acetyl iodide from the catalyst complex. Consider, for example, a typical depiction of the catalytic cycle in an acetic acid process as shown in the attached FIG. 1, wherein one of skill in the art will appreciate that modification of kinetics of the various reactions will improve production rates and quality. In particular, accelerating the reductive elimination step increases production rates of acetic acid and reduces the opportunity for aldehyde formation from the rhodium complex, resulting in a reduction of acetaldehyde-derived impurities in the final product. Such impurities are difficult, if not impossible to remove without extraordinary purification effort.

Still further features and advantages of the invention are apparent from the following description.

BRIEF DESCRIPTION OF DRAWINGS

The invention is described in detail below with reference to the appended drawings. In the Figures:

FIG. 5 is a graphical depiction of impurities produced during carbonylation (at 5 wt % water except as noted) using metal compositions according to the invention in comparison to conventional lithium iodide as a function of production rate.

DETAILED DESCRIPTION

Figure 1:
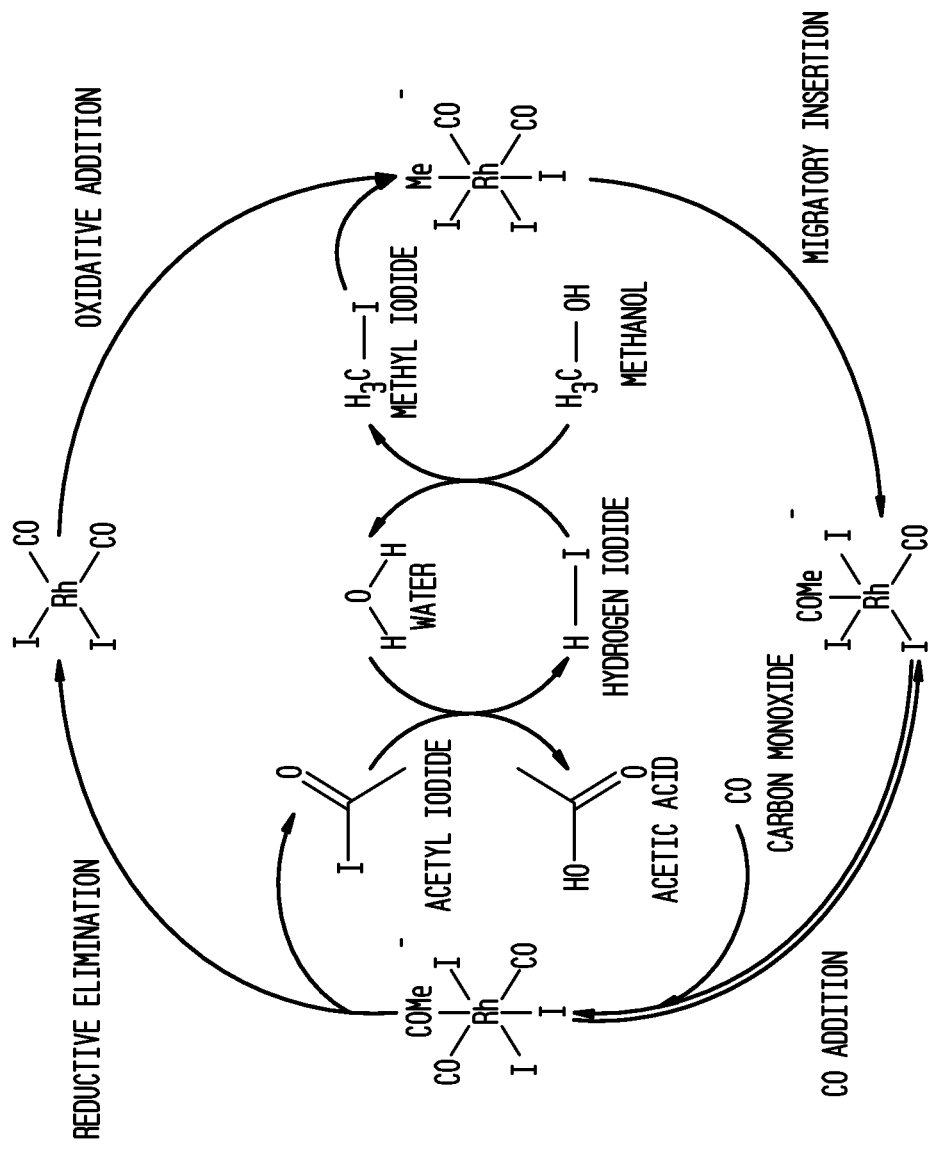
FIG. 1 is a schematic illustrating interrelated reaction paths for a typical methanol carbonylation process.

The invention is described in detail below with reference to numerous embodiments for purposes of exemplification and illustration only. Modifications to particular embodiments within the spirit and scope of the present invention, set forth in the appended claims, will be readily apparent to those of skill in the art.

Unless more specifically defined below, terminology as used herein is given its ordinary meaning. Ratios refer to molar ratios, %, ppm and like terms refer to weight percent, parts per million by weight and so forth, unless otherwise indicated.

When we refer to reaction mixtures or catalyst systems "consisting essentially of" certain components, we mean to exclude other components that would alter the basic and novel characteristics of the composition, that is, substantially change its reactivity, stability or selectivity. The language "consisting essentially of" specifically excludes unlisted salts in substantial amounts, for example, but does not exclude impurities, by-products, diluents, and so forth.

For present purposes, a metallic co-catalyst composition is considered effective as a rhodium stabilizer in the process at a given water concentration if essentially none of the rhodium catalyst metal precipitates under processing conditions in the flasher of the reaction section of a carbonylation system for a time sufficient to show characteristic stability. To test for stability, a reaction mixture may be tested under a nitrogen atmosphere in a sealed pressure glass tube at 125° C., to simulate the CO partial pressure in the flasher unit. Details of the preparation and procedure appear in U.S. Pat. No. 7,053, 241, the disclosure of which is incorporated herein by reference. In this test, sealed pressure glass tubes are equipped with controlled temperature and stirring using a pressure tube reactor system. The catalyst solutions are purged with carbon monoxide (CO) at 125° to 150° C. and a pressure of 241.1 kPa with stirring for one hour to ensure complete dissolution of the rhodium catalyst complex before conducting catalyst precipitation tests. The prepared catalyst solutions are cooled and then purged with $N_2$ for one hour to remove dissolved CO before placing the catalyst solutions into glass tubes which are sealed under a $N_2$ atmosphere. The rhodium concentration is determined by atomic absorption (AA) spectroscopy. The rhodium concentration of the solution is measured 10 minutes after the nitrogen purge is complete, or longer if so desired. Characteristic stability can also be measured by this method after 30 minutes, 1 hour, 12 hours, 24 hours, 48 hours, or more if so desired. If less than 0.5%, and preferably 0, of the rhodium precipitates, the system is considered stable, and the metal composition is deemed effective as a rhodium stabilizer. Alternatively or as additional indicia of stability, the process may be run under continuous conditions in a carbonylation unit including a flasher, preferably for 5 to 6 hours, and the flasher visually inspected for precipitation. In the experiments discussed herein, turnover in the flasher was 7.5 minutes, which is an appropriate benchmark time for stability under reduced CO partial pressure. Typically, a composition that acts primarily as a stabilizer presents a trend of decreased space-time yield in response to increased molar ratio of the metal in the composition to rhodium in the system. An increase in the molar ratio of a co-catalyst which is only a stabilizer results in an observed decrease of the space-time yield because of stabilization of rhodium by the co-catalyst, which induces a decrease of the activity of rhodium.

In some embodiments, the determination of stability is performed in a system having an amount of lithium iodide insufficient to provide stability alone. For example, an amount of lithium iodide providing a lithium:rhodium molar ratio of 38:1 represents about half of the conventional amount, and cannot provide catalyst stability at this concentration, as shown in the examples (i.e., "unstable").

A metal composition is considered effective as a rate promoter if the carbonylation rate (space-time yield, or STY defined as the g-mole acetic acid product per volume of reactor solution per time (g-mole/L/hr)) measured in acetic acid production is greater than that of the same composition without the promoter component or components. The carbonylation rate is also referred to herein as reaction productivity. Generally, to determine effectiveness of the promoter, the catalytic system is compared to a like catalyst system with the same amount of rhodium alone as the catalyst metal. In some embodiments, the catalytic system is compared to a like catalyst system with the same amount of lithium iodide co-catalyst and rhodium catalyst metal. Additional acetic acid is added to 100%. Typically, a composition that acts primarily as a rate promoter, or activator, presents a trend of increased space-time yield in response to increased molar ratio of the metal in the composition to rhodium in the system.

As used herein, a transition metal includes Group IIIB to Group IIB metals; suitable transition metals include titanium, vanadium, chromium, manganese, iron, cobalt, nickel, copper, yttrium, zirconium, molybdenum, ruthenium, lanthanum, hafnium, tungsten, and platinum. The metals of interest to this case are the transition metals discussed above as well as zinc, beryllium, aluminum, strontium, indium, tin, barium, and bismuth as well as HPA compounds discussed further below. The precise form in which a metal is used is not particularly important, provided that it is effective as a rate promoter and stabilizer, as discussed above.

As used herein, HPA refers to heteropoly acids, a class of complex proton acids made up of a metal, oxygen, an element generally from the p-block of the periodic table, and acidic hydrogen atoms. HPAs are strong Brönsted acids. A heteropoly acid is formed by condensation of two or more inorganic oxyacids comprising a coordinated element (poly atom) and a central element (hetero atom). Typically, from two to eighteen poly atoms, oxygen-linked polyvalent metal atoms, surround one or more hetero atoms. The hetero atom in the heteropoly acid may be one or more of copper, beryllium, zinc, nickel, phosphorus, silicon, boron, aluminum, germanium, gallium, iron, cerium, cobalt, arsenic, antimony, bismuth, chromium, tin, titanium, zirconium, vanadium, sulfur, tellurium, manganese, platinum, thorium, hafnium, or iodine, and the polyatom may be one or more of molybdenum, tungsten, vanadium, chromium, niobium, or tantalum, but these examples are not intended to be limiting. These acids include, but are not limited to, phosphomolybdic acid ($H_3[PO_4(MO_2O_6)_6].xH_2O$) also known as PMA, tungstosilicic acid ($H_4SiW_{12}O_{40}.H_2O$), tungstophosphoric acid ($H_3[P(W_3O_{10})_4].xH_2O$) also known as PTA, molybdosilicic acid ($H_4SiMo_{12}O_{40}.xH_2O$), molybdophosphoric acid ($H_3PMo_{12}O_{40}.xH_2O$), molybdotungstophosphoric acid ($H_3[PMo_nW_{12-n}O_{40}].xH_2O$), molybdotungstosilicic acid ($H_4[SiMo_nW_{12-n}O_{40}].xH_2O$), vanadotungstophosphoric acid ($H_{3+n}[PV_nW_{12-n}O_{40}].xH_2O$), vanadotungstosilicic acid ($H_{4+n}[SiV_nW_{12-n}O_{40}].xH_2O$), vanadomolybdosilicic acid ($H_{4+n}[SiV_nMO_{12-n}O_{40}].xH_2O$), vanadomolybdophosphoric acid ($H_{3+n}[PV_nMo_{12-n}O_{40}].xH_2O$, wherein n is an integer of 1 to 11 and x is an integer of 1 or more), tungstoboric acid ($H_5BW_{12}O_{40}$), molybdoboric acid ($H_5BMo_{12}O_{40}$) and molybdotungstoboric acid ($BH_5Mo_6O_{40}W_6$). The structures of some of the well known anions are named after the original researchers in this field. The first characterized and the best known of these is the Keggin heteropolyanion, typically represented by the formula $XM_{12}O_{40}^{x-8}$, where X is the central atom ($Se^{4+}$ or $P^{5+}$), x is its oxidation state and M is the metal ion ($Mo^{6+}$ or $W^{6+}$).

Preferably, the HPA selected comprises a phosphorus or silicon hetero atom and at least one polyatom selected from the group consisting of tungsten, molybdenum, chromium, vanadium and tantalum. The preferred HPAs may be represented by the formula $H_3M_{12}XO_{40}$, where M is the polyatom, and X is the hetero atom. Especially preferred HPAs comprise polyatoms selected from tungsten and molybdenum.

In some embodiments, a metallic co-catalyst composition is a composition comprising a lanthanide-series metal, metal compound, or metal complex. Lanthanide series metals, or lanthanons, include lanthanum, cerium, praseodymium, neodymium, promethium, samarium, europium, gadolinium, terbium, dysprosium, erbium, thulium, ytterbium, and lutetium. The precise form in which a metal is used is not particularly important, provided that it is effective as a rate promoter and stabilizer, as discussed above.

A rhodium-based catalyst system refers to a system providing a rhodium metal catalyst and an iodide promoter in a carbonylation reaction mixture.

An aqueous reaction mixture refers to a carbonylation reaction mixture comprising, for instance, water, a rhodium-based catalyst, methanol and/or methyl acetate, methyl iodide, a co-catalyst, and acetic acid.

As used herein, "reductive elimination" refers to a catalytic reaction step of a mechanistic catalyst cycle whereby the rhodium acyl carbonyl iodide complex, $[Rh(CO)_2I_3$ (COCH$_3$)]$^{1-}$, eliminates acetyl iodide from the complex to form acetyl iodide and regenerates the rhodium catalyst, [Rh(CO)$_2$I$_2$]$^{1-}$.

As used herein, "correspondent inorganic iodide" and like terminology refers to inorganic iodide attributable to the stabilizing and promoting metals added to the system in accordance with the invention. Total inorganic iodide is measured in a reaction medium by titration with an aqueous solution of silver nitrate at room temperature. Titration with silver nitrate yields a value for total inorganic halides which often consists primarily of inorganic iodides in a system according to the invention. The measurement is corrected for equilibrium HI levels and inorganic iodides attributable to any corrosion metal iodides which may be present. That is, inorganic iodide levels due to HI and corrosion metal iodides are subtracted from total iodides to determine levels of correspondent inorganic iodide attributable to the stabilizing and promoting metals added to the system in accordance with the invention. In some embodiments, total inorganic iodide is attributable to both the stabilizing and promoting metals and the reduced lithium iodide content of the reaction mixture. For present purposes "substantially less than a theoretically equivalent inorganic iodide content corresponding to the presence of a metallic co-catalyst" and like wording refers to a reaction mixture in which a metal added as a co-catalyst contributes substantially less than a theoretically equivalent amount of inorganic iodide determined by assuming that all the metal added would form a metal—iodide ionic compound. For instance, a system in accordance with the invention in which chromium is used as a stabilizing and promoting metal would result in a reaction mixture containing substantially less than three moles of inorganic iodide for each mole of chromium added (based on a Cr$^{3+}$ oxidation state). Such a reaction mixture would generally provide an actual inorganic iodide concentration upon titration of less than 75%, 70%, 65%, or 60% of the theoretically equivalent inorganic iodide concentration, and typically less than 55% or less than 50% of the theoretically equivalent inorganic iodide concentration. The reaction mixture would preferably have an actual inorganic iodide concentration of less than 40%, less than 35%, or less than 30% of the theoretically equivalent inorganic iodide concentration, and more preferably less than 20% of the theoretically equivalent inorganic iodide concentration. Even more preferably, the reaction mixture would have an actual inorganic iodide concentration of less than 15% of the theoretically equivalent inorganic iodide concentration. An inorganic iodide content of less than 90% or 80% of the equivalent amount corresponding to the metal co-catalyst added may be considered a substantial reduction in some cases.

Generally, in most cases, a concentration of correspondent inorganic iodide due to the presence of the metallic co-catalyst composition is maintained in the reactor below 5 wt % or below 4 wt %. In some embodiments, the concentration of correspondent inorganic iodide is due to the presence of the metallic co-catalyst composition and low levels of lithium iodide. Typically, the concentration of correspondent inorganic iodide due to the presence of the metallic co-catalyst composition is maintained in the reactor below 3.5 wt % or below 3 wt %. Preferably, the concentration of correspondent inorganic iodide due to the presence of the metallic co-catalyst composition is maintained in the reactor below 2.5 wt % or below 2 wt %. More preferably, the concentration of correspondent inorganic iodide due to the presence of the metallic co-catalyst composition is maintained in the reactor below 1.5 wt %. The present invention is advantageously practiced with less than 3% or less than 2% or so total inorganic iodides present in the reaction mixture from sources other than the rhodium stabilizing and rate promoting metal composition in any event to ameliorate corrosion problems and generation of undesirable by-products as noted above.

A rhodium metal catalyst may be added in any suitable form such that rhodium is in the catalyst solution as an equilibrium mixture including [RhI$_2$(CO)$_2$]$^{1-}$, as is well known in the art. When rhodium solution is in the carbon monoxide-rich environment of the reactor, solubility of the rhodium is generally maintained because rhodium/carbonyl iodide species are generally soluble in water and acetic acid. However, when transferred to carbon monoxide depleted environments as typically exist in the flasher, light ends column and so forth, the equilibrium rhodium/catalyst composition changes since less carbon monoxide is available; rhodium catalyst precipitates.

An alkyl halide, preferably methyl iodide co-catalyst/promoter (also referred to herein as an iodide promoter) is generally used in combination with the Group VIII metal catalyst component. Methyl iodide is preferred as the alkyl halide promoter. Preferably, the concentration of alkyl halide in the liquid reaction composition is in the range 1 to 50% by weight, preferably 2 to 30% by weight.

While it is preferable in most circumstances to operate with the lowest possible level of inorganic iodide, in some embodiments it is possible to operate with additional inorganic iodide which may be added in the form of iodide salts or provided by way of appropriate precursors, for example lithium acetate, as is known in the art. In most cases, the iodide salts or other inorganic iodide (anion)-generating species provide inorganic iodide in substantially a theoretical amount, as is described herein. The inorganic iodide may be generated in-situ, since under the operating conditions of the reaction system, a wide range of non-iodide precursors will react with methyl iodide to generate inorganic iodide, which acts as a catalyst stabilizer. For additional detail regarding iodide salt generation, see U.S. Pat. No. 5,001,259 to Smith et al.; U.S. Pat. No. 5,026,908 to Smith et al.; and U.S. Pat. No. 5,144,068, also to Smith et al., the disclosures of which are hereby incorporated by reference. Added or generated in-situ inorganic iodide may be used in connection with this invention as a co-catalyst or co-stabilizer with a metal co-stabilizer, but at a reduced concentration of inorganic iodide in comparison with conventional carbonylation. The inorganic iodide-providing co-catalyst may be provided in the form of a soluble salt of an alkali metal or alkaline earth metal or a quaternary ammonium or phosphonium salt. In certain embodiments, the catalyst stabilizer/co-promoter is lithium iodide, lithium acetate, or mixtures thereof. The inorganic iodide may be added as a mixture of compounds, such as a mixture of lithium iodide and sodium iodide and/or potassium iodide. See U.S. Pat. Nos. '259; '908; and '068, all to Smith et al., as referred to above. Alternatively, the inorganic iodide may be added as a precursor which generates inorganic iodide in-situ under the operating conditions of the reaction system. A wide range of non-iodide precursors which are useful include alkali metal acetates and carboxylates which will react with methyl iodide and/or HI to generate a predetermined level of inorganic iodide. The appropriate level of inorganic iodide may also be generated in-situ from non-ionic or neutral precursors, such as a phosphine oxide, arsenes, phosphines, amines, amino acids, sulfides, sulfoxides or any suitable organic ligand or ligands if so desired. Phosphine oxides, phosphines, amines, amino acids or other nitrogen or phosphorous containing compounds and suitable organic ligands generally undergo reaction readily in the presence of methyl iodide and/or HI at elevated temperatures to yield and maintain a specific level of inorganic iodide anion concentration in the reaction mixture. Useful non-iodide precursors are thus defined by their ability to maintain elevated inorganic iodide anion levels, rather than by the form in which they are added to the system. One way of introducing inorganic iodide is by incorporating suitable neutral or ionic precursor moieties such as ligands into a rhodium catalyst system as separate entities or complexed with rhodium (typically monodentate or bidentate ligands). In either case, under carbonylation conditions in the presence of methyl iodide, these free ligands, or these ligands complexed with rhodium, decompose and/or react with methyl iodide and/or HI to provide elevated levels of inorganic iodide anions. In this regard, the following Chinese References are of particular interest: Chinese Publication CN1345631; Application No. 00124639.9; Chinese Publication No. CN1105603; Application No. 94100505.4; and Chinese Publication No. CN1349855; Application No. 00130033.4. Suitable rhodium catalyst complexes which provide inorganic iodide as a co-stabilizer/promoter thus include complexes having the following structures:

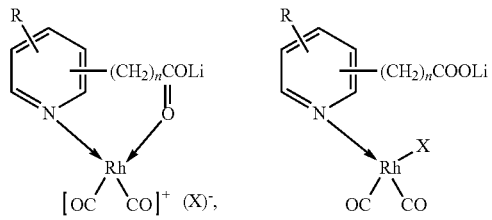

wherein R is H, or a carboxyl-containing hydrocarbon derivative; $(X^-)$ is $BPh_4^-$, $BF_4^-$, or $CH_3COO^-$; X is I, Cl, or Br; and n=0, 1, or 2. Other compounds useful as inorganic iodide-providing co-catalysts include pyridine derivatives such as:

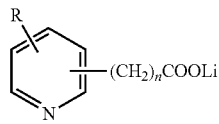

wherein R is H, or a carboxyl-containing hydrocarbon derivative, and n is 0, 1, or 2. Preferably, R is H, or e.g., lithium pyridine-2-formate, lithium pyridine-3-formate, lithium pyridine-4-formate, lithium pyridine-2-acetate, lithium pyridine-3-acetate, lithium pyridine-4-acetate, or lithium pyridine-3-propionate. One of skill in the art will appreciate that a great many other components may be used to generate inorganic iodide.

The metallic co-catalyst compositions of the invention may be added to the reaction mixture in any suitable form, preferably wherein the promoter metal is in a non-zero oxidation state. Following are exemplary chromium salts: $Cr(OH)_3.3H_2O$, $CrCl_2$, $CrCl_3.6H_2O$, $CrI_2$, $CrBr_2$, $CrI_3.9H_2O$, $CrBr_3.6H_2O$, $CrO_3$, $Cr_2O_3$, $CrPO_4.6H_2O$, $Cr(OCOCH_3)_3$, $Cr(NO_3)_3.9H_2O$, $CrCO_3$, $Cr(OCOCH_3)_2$. Further details as to suitable chromium compounds are found in Pauling L., General Chemistry, Chapter 22 pp. 722-740 Dover (1988), the disclosure of which is incorporated herein by reference. Similar forms are suitable for nickel, iron, molybdenum, bismuth, tin, zinc, yttrium, ruthenium, lanthanum, and beryllium. Exemplary lanthanum salts include: $La(C_2H_4O_2)_3.H_2O$; LaSb; LaAs; $LaI_3$; $La_2(CO_3)_3.8H_2O$; $La_2(O:C_6Cl_2O_2:O)_3.xH_2O$; $LaCl_3.7H_2O$; $LaF_3$; $La(NO_3)_3.6H_2O$; $La_2(C_2O_4)_3.9H_2O$; $La_2O_3$; LaP; and $La_2(SO_4)_3.9H_2O$. Similar forms are suitable for cerium, praseodymium, neodymium, and the remaining lanthanide series metals. Further details as to suitable lanthanide compounds are found in the Kirk-Othmer Encyclopedia of Chemical Technology, Third Edition, Vol. 19, pp. 833-854, John Wiley & Sons (1982). All precursors capable of forming the active species are preferred. Acetate, chloride, iodide, carbonyl, and nitrate forms are particularly preferred.

A preferred carbonylation apparatus or process generally includes at least a reactive section, including a reactor and a flash vessel, and a purification section. The apparatus of the present invention is used in connection with the carbonylation of methanol, and/or its reactive derivatives, with carbon monoxide in a homogeneous catalytic reaction system comprising a reaction solvent (typically acetic acid), methanol and/or its reactive derivatives, a soluble rhodium catalyst and at least a finite concentration of water. The carbonylation reaction proceeds as methanol and carbon monoxide are continuously fed to the reactor. The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in-situ by the water gas shift reaction is preferably kept low, for example, less than 1 bar partial pressure, as its presence may result in the formation of hydrogenation products. The partial pressure of carbon monoxide in the reaction is suitably in the range 1 to 70 bar, preferably 1 to 35 bar, and most preferably 1 to 15 bar.

The pressure in the carbonylation reactor is suitably in the range 10 to 200 bar, preferably 10 to 100 bar, most preferably 15 to 70 bar. The temperature of the carbonylation reaction is suitably in the range 100 to 300° C., preferably in the range 125 to 220° C. Acetic acid is manufactured in a liquid phase reaction at a temperature of from about 150-200° C. and a pressure of from about 30 to about 60 bar in typical embodiments wherein acetic acid is utilized in the reaction mixture as the solvent for the reaction.

The reaction mixture is fed to a flash vessel at reduced pressure to flash off product and light ends. The pressure in the flash vessel is generally less than 2 or 3 bar and usually less than 1 bar. Less than 1 bar carbon monoxide partial pressure is also typical in the flash vessel. Less than 0.5 bar or 0.25 bar carbon monoxide partial pressure is used in flash vessels of commercial production units.

Suitable reactive derivatives of methanol include methyl acetate and dimethyl ether. A mixture of methanol and reactive derivatives thereof may be used as reactants in the process of the present invention. Preferably, methanol and/or methyl acetate are used as reactants. At least some of the methanol and/or reactive derivative thereof will be converted to, and hence present as, methyl acetate in the liquid reaction composition by reaction with acetic acid product or solvent. The concentration in the liquid reaction composition of methyl acetate is suitably in the range 1 to 70% by weight, preferably 1 to 50% by weight, most preferably 2 to 35% by weight.

Water may be formed in-situ in the liquid reaction composition, for example, by the esterification reaction between methanol reactant and acetic acid product. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. Preferably, the concentration of water in the liquid reaction composition is in the range 0.1 to 16% by weight, more preferably 0.1 to 14% by weight, even more preferably 0.1 to 10% by weight, and most preferably 1 to 8% by weight. In some embodiments, the concentration of water in the liquid reaction composition is generally in the range of 0.1 to 10 wt %, typically 0.2 to 5 wt %, preferably 0.5 to 3 wt %, more preferably 0.5 to 2.5 wt %, even more preferably 0.75 to 2.5 wt %, and most preferably 1.5 to 2.5 wt %.

The reaction liquid is typically drawn from the reactor and flashed. The crude vapor product stream from the flasher is sent to a purification system which generally includes a light ends column and a dehydration column, and optionally further purification if required. The carbonylation system may use only 2 purification columns and is preferably operated as described in more detail in U.S. Pat. No. 6,657,078 to Scates et al., entitled "Low Energy Carbonylation Process", the disclosure of which is incorporated herein by reference.

Figure 2:
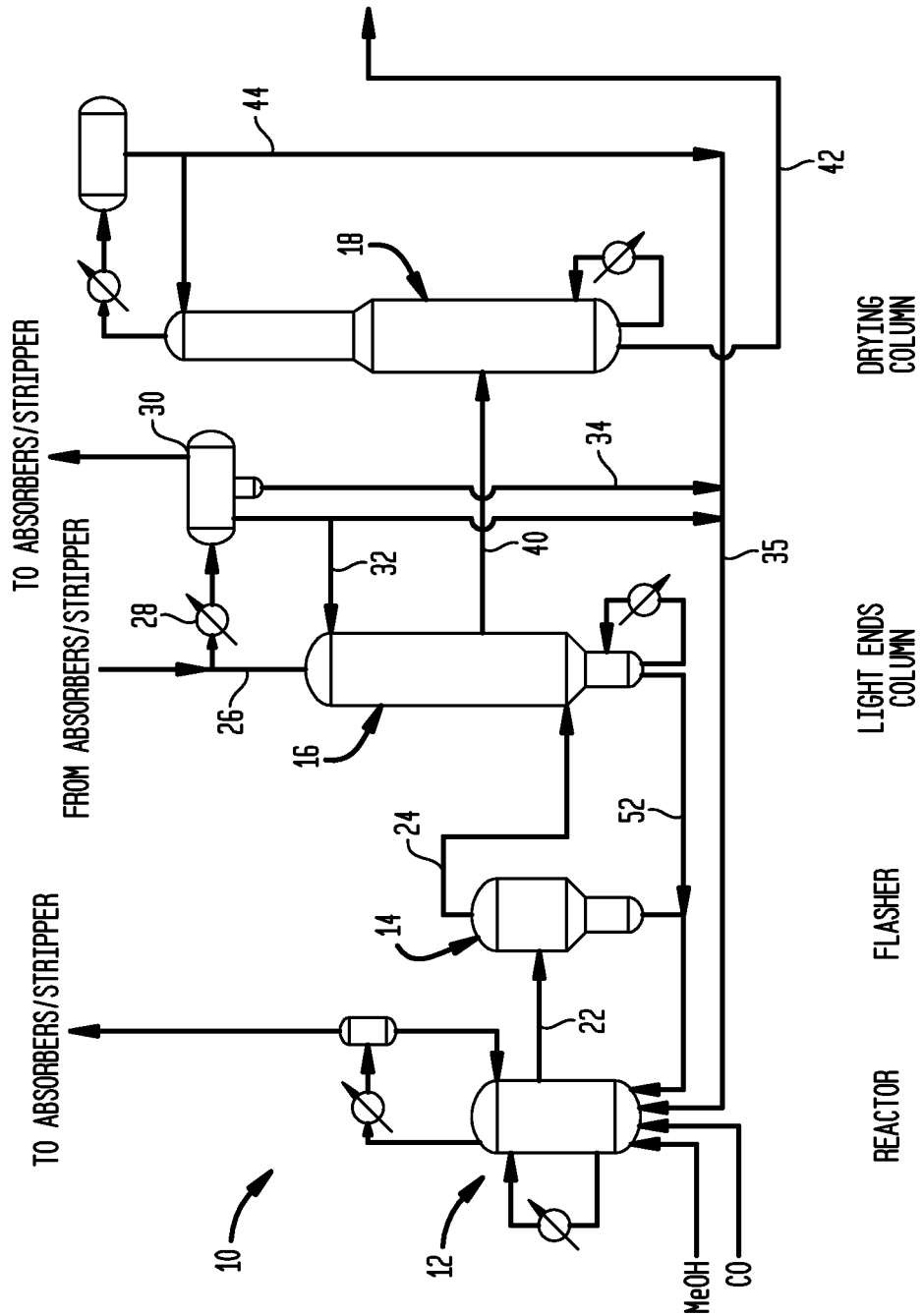
FIG. 2 is a schematic diagram of an apparatus suitable for practicing the process of the present invention.

Referring to FIG. 2, there is shown a carbonylation unit 10 of the class utilized in connection with the present invention. Unit 10 includes a reactor 12, a flasher 14, a light ends column 16, a drying or dehydration column 18 as well as optionally further purification, such as a heavy ends column to remove higher boiling impurities (not shown). Reactor 12 includes the reaction medium and there is fed thereto methanol and carbon monoxide. A portion of the reaction medium is continuously provided to flasher 14 via line 22 where crude product is flashed and sent to light ends column 16 via line 24 as a hot vapor feed.

In column 16, the product is purified of light components which exit the column via line 26, are condensed in a first condenser 28 and then decanted in a decanter 30. Conventionally, the light phase from decanter 30 is refluxed to column 16 via line 32, while the heavy phase from decanter 30 is returned to the reactor via lines 34, 35. Also provided, but not shown, are absorbers and strippers used to recycle material into the system.

A purified product stream 40 is withdrawn as a (preferably liquid) side stream from column 16 and fed to drying column 18 where water is removed from the partially purified product. Product is withdrawn via line 42. If necessary, further purification may be done. The overhead and some product acetic acid is used as reflux for column 18 or recycled to the reactor via line 44.

Column 16 generates a liquid residue stream 52 which is conventionally recycled with flasher residue to the reactor as shown.

EXAMPLES

Comparative Experiments

Utilizing a pilot scale apparatus simulating the reactor and flasher of the class described above in connection with FIG. 2, a lithium iodide promoted carbonylation system was compared with a metal promoted system of the invention. Specifically, $Rh(OAc)_3$ (1000 ppm Rh) was introduced into a reactor such as reactor 12 with $AcOH/H_2O/HI$; the mixture was pressurized under 5 bar of CO at 140° C. during a 1 hour preformation step. The temperature was then increased in the reactor to 190° C. At that time methyl acetate, methyl iodide and the carbonylation catalyst precursor were introduced from a feed tank into the reactor. In a flash vessel such as that shown as flasher 14 of FIG. 2, a mixture of $H_2O/AcOMe/MeI/AcOH$ was heated to 140° C. When the temperature of the reactor reached 190° C. and the flasher reached 140° C., carbon monoxide and methanol were fed to the reactor along with recycled catalyst solution condensed from the base of the flasher, and the carbonylation reaction began. The flasher volume was replaced every 7.5 minutes at the circulation rates employed. Acetic acid product, water, methyl acetate and methyl iodide were condensed and collected from the flasher overhead. The continuous carbonylation process was operated for at least one hour. The reaction rate was determined by CO uptake measured in the reactor and by the amount of acetic acid collected in the vapor condensed flasher overhead material. The stability of the catalyst system was evaluated by measuring the amount of catalyst precipitation in the flasher base after the continuous operation was complete.

Further experimental details and results appear in Table 1 below and in FIG. 3.

TABLE 1

Comparison of Lithium Iodide versus Chromium Promoted Methanol Carbonylation

| | Rh/LiI system Experiment 1A | Rh/Cr system Experiment 1B |
|---|---|---|
| Rh reactor concentration (ppm) | 989 | 1000 |
| Chromium reactor concentration (ppm) | | 10 100 |
| Chromium/rhodium reactor molar ratio | | 20 |
| Lithium/rhodium reactor molar ratio | 77.1 | |
| Lithium reactor concentration (ppm) | 5183 | |
| Water reactor concentration (% wt) | 4.2 | 3.8 |
| Acetic Acid concentration (% wt) | 75.8 | 79 |
| Methyl iodide concentration (% wt) | 9.7 | 10.7 |
| Methyl Acetate concentration (% wt) | 1 | 2 |
| Methanol feed rate | 1.5 g/min | 1.5 g/min |
| Reactor Temperature (° C.) | 190 | 190 |
| Flasher Temperature (° C.) | 142 | 140-141 |
| Time of the experiment (minutes) | 500 | 540 |
| Carbonylation Rate (CO), mol/L/hr | 17.3 | 17.3 |
| Carbonylation Rate (AcOH), mol/L/hr | 17.8 | 18.3 |
| Iodide reactor concentration (wt %) | 9.4 | 0.8 |
| Catalyst precursor used | $Rh(OAc)_3$, 5 wt % | $Rh(OAc)_3$, 5 wt % |
| Co catalyst precursor used | LiI | $Cr(OAc)_3$ |

Note:

Two carbonylation rates, one determined by carbon monoxide uptake and one determined by quantified acetic acid product, are used to validate the results by similarity. A third carbonylation rate measuring MeOH consumed may also be used. The 989 ppm Rh concentration is comparable to 1000 ppm used in subsequent experiments. The 77.1 LiI molar ratio is comparable to the 76 ratio used in many subsequent experiments.

Figure 3:
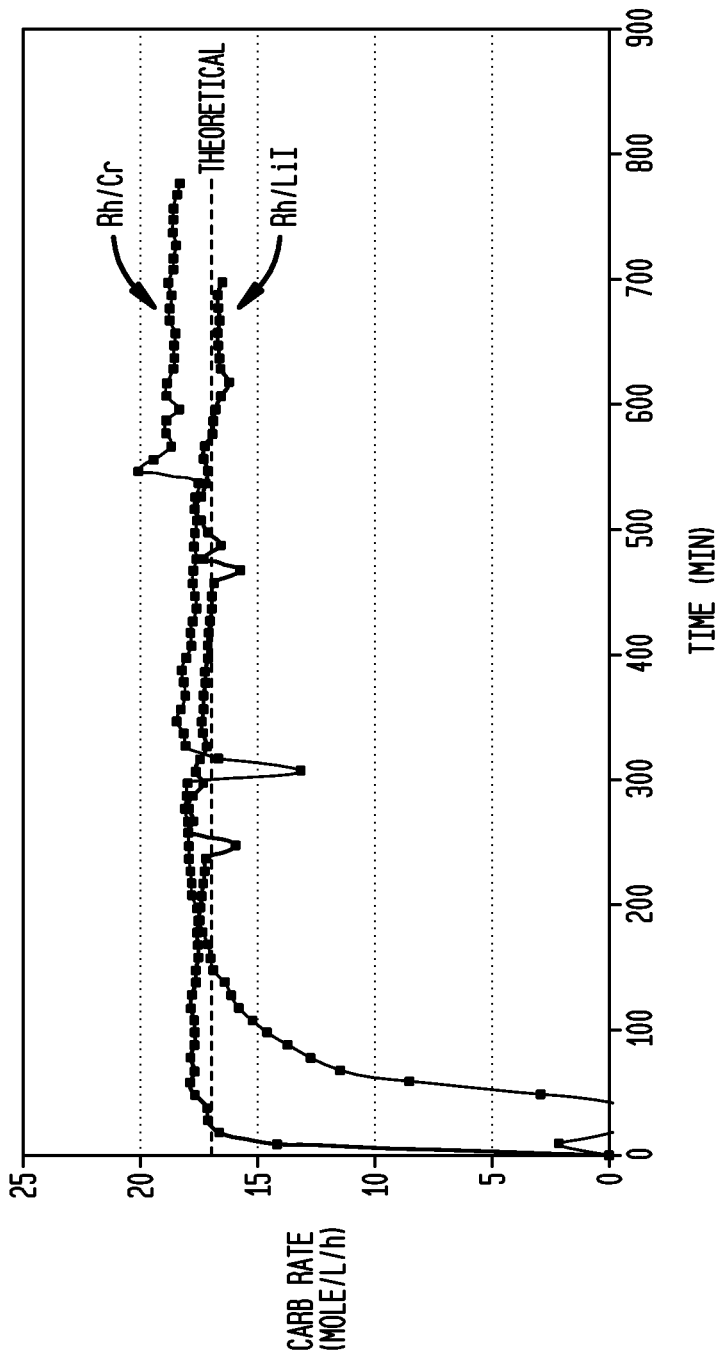
FIG. 3 is a plot of carbonylation rate versus time for a Rh/Li catalyst system and a Rh/Cr catalyst system.

It will be appreciated from Table 1 and FIG. 3 that under similar conditions, the chromium promoted system of the invention exhibited very similar performance to a lithium iodide stabilized and promoted system. Several advantages are noted, however, including the fact that the metallic promoter/rhodium molar ratios of the present invention may be substantially lower than lithium/rhodium molar ratios by a lithium iodide promoted system. Consequently, the inorganic iodide level is substantially lower in the chromium/rhodium system. This feature is believed to make it possible to run the process with less by-product generation than with conventional promoters.

We have found by titration of the reactor solution with silver nitrate that inorganic iodide levels are extremely low, i.e., 0.7-1.5 wt %, when using chromium as a rate promoter/catalyst stabilizer.

It is seen from the data in Table 1 that substituting a stabilizing and promoting metal for lithium iodide provides surprising stability and production rates (STY). Further examples demonstrate like results for other compositions of interest.

Example Series AA

Following generally the procedures noted above, further experiments were performed demonstrating an unstabilized rhodium system at a variety of water concentrations, and a lithium iodide-stabilized system at a variety of lithium iodide:rhodium molar ratios and water concentrations. In the examples below, except as otherwise noted, the conditions were as follows. Methyl iodide was added at a concentration of 10 wt %, and methyl acetate controlled at a concentration of 2%. Rhodium concentrations were 1000 ppm in the reactor. In each case, the balance of the reaction mixture at the start of the reaction was made up of acetic acid. Water concentrations ranged from 3 to 8%. With the exception of the rhodium tests without a co-catalyst, the metallic co-catalyst to rhodium molar ratio ranged from 0.5:1 to 115:1. The ratios provided are on a molar basis.

All the tests discussed immediately below were performed at reaction conditions of 190° C. and 30 bar total pressure. The methanol carbonylation reaction was allowed to proceed from about 2 hours to 9 hours.

Runs 2A-2C were operated using rhodium catalyst with no stabilizers (lithium iodide or other) added.

TABLE 2

Rhodium-catalyzed acetic acid production (no stabilizer or promoter present)

| Run | $H_2O$ (wt %) | Time run (hr) | STY (mol/l/hr) | Stability by visual observations |
|---|---|---|---|---|
| 2A | 8 | 3 | 10.5 | Unstable (small amounts of Rh precipitate into the flasher and the reactor) |
| 2B | 6 | 2 | 6.6 | Unstable (Precipitation of Rh into the flasher and the reactor) |
| 2C | 3 | 3 | 5.4 | Unstable (large amounts of Rh precipitate into the flasher and the reactor) |

Rh species were preformed from $Rh(OAc)_3$, at 10 wt % $H_2O$, 1 wt % HI and 89 wt % AcOH at 140° C. and 5 bar CO partial pressure for 1 hour. No stabilizer was introduced. Table 2 indicates that the methanol carbonylation reaction rate decreases with a decrease in reactor water concentration, which is well known to those skilled in the art. Also, in the absence of a rhodium catalyst stabilizer, rhodium precipitation increases as the water decreases.

TABLE 3

Acetic acid production co-catalyzed with lithium iodide.

| Run | Rh/LiI Ratio | $H_2O$ (wt %) | Time run (hr) | STY (mol/l/hr) | Stability by visual observations |
|---|---|---|---|---|---|
| 3A | 1/15 | 5 | 2.5 | 11.6 | Unstable (Precipitation of Rh into the flasher and the reactor) |
| 3B | 1/76 | 6 | 3 | 17.2 | Stable (No Rh precipitation) |
| 3C | 1/76 | 5 | 7 | 17.9 | Stable (No Rh precipitation) |
| 3D | 1/115 | 5 | 9 | 17.8 | Stable (No Rh precipitation) |

For experiments presented in Table 3, Rh species were preformed as described for Table 2. LiI was introduced in the flasher medium before this material was recycled to the reactor during the beginning of the experiment prior to methanol carbonylation. When the methanol carbonylation reaction began, the concentration of water in the reactor was about 9%. The concentration of water decreased to 5-6% after 1 hour and this water concentration was maintained through the remainder of the experiment.

Table 3 shows lithium iodide over a wide range of metal/Rh ratios and over a range of water concentrations. In sufficient amounts lithium iodide stabilizes rhodium effectively. Note that the reaction rate is influenced by the lithium iodide. These observations demonstrate the prior art of methanol carbonylation by rhodium promotion and stability by iodide salts.

Experiments with Rhodium and a Single Metal (No Inorganic Iodide-providing Co-catalyst Such as Lithium Iodide was Used)

Following generally the procedures noted above, tin, yttrium, chromium and so forth were tested to determine their suitability as promoters and stabilizers. In the examples below, except as otherwise noted, the conditions were as follows. Methyl iodide was added at a concentration of 10 wt %, and methyl acetate controlled at a concentration of 2%. Rhodium concentrations were 1000 ppm in the reactor. In each case, the balance of the reaction mixture at the start of the reaction was made up of acetic acid. Water concentrations ranged from 3 to 6%. The metallic co-catalyst to rhodium molar ratio ranged from 0.5:1 to 50:1. The ratios provided are on a molar basis.

All the tests discussed immediately below were performed at reaction conditions of 190° C. and 30 bar total pressure. The methanol carbonylation reaction was allowed to proceed from about 1 hour to about 24 hours.

It is seen from the data in the following tables that substituting certain stabilizing and promoting metals for lithium iodide provides surprising stability and production rates (STY).

TABLE 4

Acetic acid production co-catalyzed with tin.

| Run | Rh/Sn Ratio | $H_2O$ (wt %) | Co-catalyst | Time run (hr) | STY (mol/l/hr) | Stability by visual observations |
|---|---|---|---|---|---|---|
| 4A | 1/0.5 | 3 | $SnI_4$ | 3 | 15 | Stable (No Rh precipitation but Sn deposit at the top of the flasher) |
| 4B | 1/1 | 6 | $SnI_4$; $SnI_2$ | 7.5 | 11.5 | Stable (No Rh precipitation but Sn deposit at the top of the flasher) |
| 4C | 1/3 | 6 | $SnI_4$; $SnI_2$ | 4.3 | 11.2 | Stable (No Rh precipitation but Sn |

TABLE 4-continued

Acetic acid production co-catalyzed with tin.

| Run | Rh/Sn Ratio | H$_2$O (wt %) | Co-catalyst | Time run (hr) | STY (mol/l/hr) | Stability by visual observations |
|---|---|---|---|---|---|---|
| 4D | 1/10 | 6 | SnI$_4$; SnI$_2$ | 7.5 | 9.6 | deposit at the top of the flasher) Stable (No Rh precipitation but Sn deposit at the top of the flasher) |

For the first test with SnI$_4$ as described in Table 4, the only co-metal stabilizer/promoter, SnI$_4$ was introduced with MeI and AcOMe into the reactor with the rhodium catalyst after the preformation step of the active Rh species in the reactor. At this initial time of the experiment, the concentration of water in the reactor was about 9%. Once the methanol carbonylation reaction began, the concentration of water decreased to 3% after 1 hour and this water concentration was maintained through the remainder of the experiment. For the remaining tests, after the preformation of the active Rh species in the reactor, SnI$_4$ and SnI$_2$ were introduced directly into the reactor after cooling and depressurizing the reactor. At this time, the concentration of water in the reactor was about 9%. The reactor was then heated and the methanol carbonylation reaction began. During the run, the concentration of water decreased to 5-6% after 1 hour and this water concentration was maintained through the remainder of the experiment.

Comparing tests of rhodium catalyst systems for Rh with no co-metal with Rh/LiI at a 1/76 molar ratio at 3 wt % water as provided in Table 3 and with Rh/Sn at a 1/0.5 molar ratio as provided in Table 4, Sn stabilized Rh at a lower metal to rhodium molar ratio, but tin was deposited at the top of the flasher. As a result, the acetic acid production rate decreased. Sn is considered primarily a stabilizer because an increase in the molar ratio of Sn results in a decrease of the STY.

TABLE 5

Acetic acid production co-catalyzed with chromium.

| Run | Rh/Cr Ratio | H$_2$O (wt %) | Co-catalyst | Time run (hr) | STY (mol/l/hr) | Stability by visual observations |
|---|---|---|---|---|---|---|
| 5A | 1/50 | 6 | CrCl$_3$•6H$_2$O | 4.5 | 16.7 | Unstable (Solubility concerns of Cr |
| 5B | 1/40 | 6 | CrCl$_3$•6H$_2$O | 13 | 15.4 | Unstable (Solubility concerns of Cr) |
| 5C | 1/30 | 6 | CrCl$_3$•6H$_2$O | 24.3 | 15 | Unstable (Solubility concerns of Cr) |
| 5D | 1/20 | 6 | CrCl$_3$•6H$_2$O | 9 | 17.5 | Stable (No Rh precipitation and no solubility concerns of Cr) |
| 5E | 1/10 | 6 | CrCl$_3$•6H$_2$O | 6 | 17.2 | Stable (No Rh precipitation and no solubility concerns of Cr) |
| 5F | 1/20 | 5 | CrCl$_3$•6H$_2$O | 9.5 | 18 | Stable (No Rh precipitation and no solubility concerns of Cr) |
| 5G | 1/20 | 4 | CrCl$_3$•6H$_2$O | 6 | 15.3 | Unstable (solubility concerns of Cr at low water concentration) |
| 5H | 1/50 | 3 | CrCl$_3$•6H$_2$O | 5.8 | 10.3 | Unstable (solubility concerns of Cr at low water concentration) |
| 5I | 1/40 | 3 | CrCl$_3$•6H$_2$O | 2.6 | 11.2 | Unstable (solubility concerns of Cr at low water concentration) |
| 5J | 1/30 | 3 | CrCl$_3$•6H$_2$O | 5 | 12 | Unstable (solubility concerns of Cr at low water concentration) |

For experiments presented in Table 5, CrCl$_3$.6H$_2$O was introduced in water solution through a feed tank into the reactor after the preformation of the active Rh species in the reactor at the beginning of the reaction. At this time, the concentration of water in the reactor was about 18%. Then the methanol carbonylation reaction began and the concentration of water decreased to 5-6% after 2 hours and this water concentration was maintained through the remainder of the experiment. During this time the inorganic iodide concentration was less than about 1.5 wt %, which indicates that at high Cr concentration, the form of the Cr salt present was not as an iodide salt, which confirms the rhodium stability by the Cr co-metal and not by a high inorganic iodide concentration.

Comparing Rh/LiI at a 1/76 molar ratio and 3 or 5 wt % water with Rh/Cr at a 1/20 molar ratio and 5% water, the Cr stabilizes Rh at an effective level as for LiI, yet at a much lower inorganic iodide concentration, while achieving the same carbonylation rates. The chromium co-metal is an effective rhodium stabilizer/promoter. It is clear that this effect is contributed primarily by the co-metal alone and not by an iodide salt, since the total iodide concentration in the reactor medium during these experiments was less than 1 wt %, which is close to the equilibrium concentration of HI. See the iodide titration results provided in Examples 30B and E, below.

TABLE 6

Acetic acid production co-catalyzed with yttrium.

| Run | Rh/Y Ratio | H$_2$O (wt %) | Co-catalyst | Time run (hr) | STY (mol/l/hr) | Stability by visual observations |
|---|---|---|---|---|---|---|
| 6A | 1/40 | 6 | YCl$_3$•6H$_2$O | 5 | 16 | Unstable (solubility concerns of Y and Rh precipitation) |
| 6B | 1/15 | 5 | Y(OAc)$_3$•xH$_2$O | 4.5 | 16.5 | Unstable (solubility concerns of Y and Rh precipitation) |
| 6C | 1/10 | 5 | Y(OAc)$_3$•xH$_2$O | 3.3 | 12 | Unstable (solubility concerns of Y and Rh precipitation) |

For the first test in Table 6, $YCl_3 \cdot 6H_2O$ was introduced in water solution through a feed tank into the reactor after the preformation of the active Rh species in the reactor (at the beginning of the reaction; see discussion at Table 2). At this time (with the addition of Y salts in water), the concentration of water in the reactor was about 30%. For the two remaining tests in Table 6, when the preformation of Rh species in the reactor was finished (see discussion at Table 2), $Y(OAc)_3$ was introduced directly into the reactor (after cooling and depressurizing the reactor). The reactor was then heated. At this time (after the addition of Y salts in water), the concentration of water in the reactor was about 15%. For all three tests, the methanol carbonylation reaction then began, and the concentration of water decreased to 5-6% after 2 hours and this water concentration was maintained through the remainder of the experiment. During this time Rh—Y complexes were forming.

Y is a good co-catalyst in terms of activity, but has solubility concerns in the medium allowing the non-stability of Rh. Therefore, yttrium is considered primarily a rate promoter.

TABLE 7

Acetic acid production co-catalyzed with nickel.

| Run | Rh/Ni Ratio | $H_2O$ (wt %) | Co-catalyst | Time run (hr) | STY (mol/l/hr) | Stability by visual observations |
|---|---|---|---|---|---|---|
| 7A | 1/5 | 6 | $Ni(OAc)_2 \cdot 4H_2O$ | 2.5 | 8.7 | Stable (No Rh precipitation) |
| 7B | 1/15 | 6 | $Ni(OAc)_2 \cdot 4H_2O$ | 2.5 | 9.3 | Stable (No Rh precipitation) |
| 7C | 1/30 | 6 | $Ni(OAc)_2 \cdot 4H_2O$ | 1.5 | 5 | Stable (No Rh precipitation) |

For experiments presented in Table 7, when the preformation of the active Rh species in the reactor was finished (see discussion at Table 2), $Ni(OAc)_2 \cdot 4H_2O$ was introduced in solution in water through a feed tank into the reactor. At this time (with the addition of Ni salts in water), the concentration of water in the reactor was about 15%. Then the methanol carbonylation reaction began and the concentration of water decreased to 5-6% after 2 hours and this water concentration was maintained through the remainder of the experiment.

As Table 7 shows, nickel provided rhodium stability to the system, but did not achieve good production rates. Nickel acts as a mild rate promoter. High levels of nickel composition were insufficiently soluble to further promote the reaction rate. Nickel complexes pre-formed prior to introduction to the reactor may be suitable for use with water concentrations of 5 wt % or below. Suitable amounts include a nickel content of 10, 15, or 20 times the amount of rhodium present on a molar basis.

TABLE 8

Acetic acid production co-catalyzed with zirconium.

| Run | Rh/Zr Ratio | $H_2O$ (wt %) | Co-catalyst | Time run (hr) | STY (mol/l/hr) | Stability by visual observations |
|---|---|---|---|---|---|---|
| 8A | 1/15 | 6 | $ZrCl_4$ | 3 | 9.3 | Unstable (Solubility concerns of Zr) |

For the experiment presented in Table 8, when the preformation of Rh species in the reactor was finished (see discussion at Table 2), $ZrCl_4$ was introduced in solution in water through a feed tank into the reactor. At this time (with the addition of Zr salts in water), the concentration of water in the reactor was about 15%. Then the methanol carbonylation reaction began and the concentration of water decreased to 5-6% after 2 hours and this water concentration was maintained through the remainder of the experiment.

Solubility of Zr salts was insufficient to provide rhodium stability or good production rates in this test.

TABLE 9

Acetic acid production co-catalyzed with iron.

| Run | Rh/Fe Ratio | $H_2O$ (wt %) | Co-catalyst | Time run (hr) | STY (mol/l/hr) | Stability by visual observations |
|---|---|---|---|---|---|---|
| 9A | 1/15 | 6 | $FeI_2$ | 3 | 10.8 | Unstable (Solubility concerns of Fe) |
| 9B | 1/6 | 6 | $FeCl_3$ | 2 | 8.2 | Unstable (Solubility concerns of Fe) |

For experiments presented in Table 9, for the first test, when the preformation of the active Rh species in the reactor was finished (see discussion at Table 2), $FeI_2$ was introduced directly into the reactor (after cooling and depressurizing). At this time, the concentration of water in the reactor was about 9%. For the second test, when the preformation of Rh species in the reactor was finished (see discussion at Table 2), $FeCl_3$ was introduced in solution in water through a feed tank into the reactor. At this time (with the addition of Fe salts in water), the concentration of water in the reactor was about 11%. For both tests, the methanol carbonylation reaction then began and the concentration of water decreased to 5-6% after 1 hour and this water concentration was maintained through the remainder of the experiment.

Solubility of Fe salts was insufficient to provide good rhodium stability or production rates in these tests. However, $FeI_2$ in an Rh/Fe molar ratio of 1/15 provided about the same results as lithium iodide at the same molar ratio. Iron complexes pre-formed prior to introduction to the reactor may be suitable for use with water concentrations of 5 wt % or below. Suitable amounts include an iron content of 10, 15, or 20 times the amount of rhodium present on a molar basis.

TABLE 10

Acetic acid production co-catalyzed with molybdenum.

| Run | Rh/Mo Ratio | $H_2O$ (wt %) | Co-catalyst | Time run (hr) | STY (mol/l/hr) | Stability by visual observations |
|---|---|---|---|---|---|---|
| 10A | 1/10 | 4 | $Mo(CO)_6$ | 2 | 7 | Unstable (Solubility concerns of Mo) |
| 10B | 1/15 | 6 | $Mo(CO)_6$ | 3 | 7 | Unstable (Solubility concerns of Mo) |
| 10C | 1/20 | 6 | $Mo(CO)_6$ | 3 | 18.5 | Unstable (Solubility concerns of Mo) |
| 10D | 1/20 | 6 | $MoCl_3$ | 2.5 | 11.5 | Unstable (Solubility concerns of Mo) |

For experiments presented in Table 10, when the preformation of the active Rh species in the reactor was finished (see discussion at Table 2), Mo(CO)$_6$ or MoCl$_3$ was introduced directly into the reactor (after cooling and depressurizing). At this time, the concentration of water in the reactor was about 9%. Then the methanol carbonylation reaction began and the concentration of water decreased to 5-6% after 1 hour and this water concentration was maintained through the remainder of the experiment.

Solubility of Mo salts was insufficient to provide rhodium stability to the system. However, molybdenum in the [Mo(CO)$_6$] form did provide a good production rate at an Rh/Mo molar ratio of 1/20. Molybdenum complexes pre-formed prior to introduction to the reactor may be suitable for use with water concentrations of 5 wt % or below. Suitable amounts include a molybdenum content of 5, 10, or 15 times the amount of rhodium present on a molar basis.

TABLE 11

Acetic acid production co-catalyzed with indium.

| Run | Rh/In Ratio | H$_2$O (wt %) | Co-catalyst | Time run (hr) | STY (mol/l/hr) | Stability by visual observations |
|---|---|---|---|---|---|---|
| 11A | 1/1 | 6 | InI$_3$ | 2 | 3.9 | Unstable (Rh precipitation) |
| 11B | 1/5 | 6 | InI$_3$ | 2 | 12 | Unstable (Rh precipitation) |
| 11C | 1/18 | 6 | InI$_3$ | 2 | 9.8 | Unstable (Rh precipitation) |

For experiments presented in Table 11, InI$_4^-$ was synthesized from InI$_3$ with HI in AcOH solution. When the preformation of the active Rh species in the reactor was finished (see discussion at Table 2), InI$_4^-$ species was introduced through a feed tank into the reactor. At this time, the concentration of water in the reactor was about 11%. Then the methanol carbonylation reaction began and the concentration of water decreased (to 5-6%) after 1 hour and this water concentration was maintained through the remainder of the experiment.

Indium failed to provide rhodium stability or good production rates in the tests described in Table 11.

TABLE 12

Acetic acid production co-catalyzed with ruthenium.

| Run | Rh/Ru Ratio | H$_2$O (wt %) | Co-catalyst | Time run (hr) | STY (mol/l/hr) | Stability by visual observations |
|---|---|---|---|---|---|---|
| 12A | 1/2 | 5 | RuI$_3$ | 3 | 8 | Unstable (Rh precipitation) |
| 12B | 1/5 | 5 | RuI$_3$ | 5 | 11 | Stable (No Rh precipitation) |

For experiments presented in Table 12, at a Rh/Ru molar ratio of greater than 1/2 (e.g., 1/5), the system achieves rhodium stability, but only at low rates. Therefore, ruthenium is considered primarily a stabilizer.

When preformation of the active Rh species in the reactor is finished (see discussion at Table 2), RuI$_3$ is introduced directly into the reactor (after cooling and depressurizing the reactor) in the form of [RuI$_3$(CO)$_3$]$^-$.

TABLE 13

Acetic acid production co-catalyzed with tungsten.

| Run | Rh/W Ratio | H$_2$O (wt %) | Co-catalyst | Time run (hr) | STY (mol/l/hr) | Stability by visual observations |
|---|---|---|---|---|---|---|
| 13A | 1/20 | 6 | WCl$_3$ | 1 | 9 | Unstable (solubility concerns of W) |

For the experiment presented in Table 13, when preformation of the active Rh species in the reactor was finished (see discussion at Table 2), WCl$_3$ was introduced directly into the reactor (after cooling and depressurizing the reactor). Tungsten did not achieve rhodium stability in an Rh/W ratio of 1/20.

TABLE 14

Acetic acid production co-catalyzed with lanthanum.

| Run | Rh/La Ratio | H$_2$O (wt %) | Co-catalyst | Time run (hr) | STY (mol/l/hr) | Stability by visual observations |
|---|---|---|---|---|---|---|
| 14A | 1/20 | 6 | LaCl$_3$•xH$_2$O | 8.5 | 14 | Stable (No Rh precipitation) |
| 14B | 1/30 | 6 | LaCl$_3$•xH$_2$O | 9.6 | 15 | Stable (No Rh precipitation) |
| 14C | 1/40 | 5 | LaCl$_3$•xH$_2$O | 3 | 14.8 | Unstable (Solubility concerns with La) |

For experiments presented in Table 14, when the preformation of the active Rh species in the reactor was finished (see discussion at Table 2), LaCl$_3$ was introduced directly into the reactor (after cooling and depressurizing the reactor).

Lanthanum provides stability to rhodium in Rh/La molar ratios of less than 1/40 and promotes the production rate (STY).

In summary, tin, ruthenium, nickel and chromium in effective amounts provided catalyst stability. Tin and chromium also provided STYs above 12, as did yttrium, molybdenum, and barium in effective amounts, although yttrium, molybdenum, and barium did not impart catalyst stability.

Zinc, bismuth, and beryllium are also believed suitable for use with water concentrations of 5 wt % or below. Suitable amounts for zinc (for example, Zn(OAc)$_2$.2H$_2$O) include 0.5, 5, or 10 times the amount of rhodium present on a molar basis. Suitable amounts for bismuth (for example, Bi(OAc)$_3$) include 10 or 20 times the amount of rhodium present on a molar basis. Suitable amounts for beryllium (for example, BeCl$_2$) include 10, 15, or 20 times the amount of rhodium present on a molar basis.

Experiments with Rhodium and a Binary Metal Co-catalyst, No Lithium Iodide

Following generally the procedures noted above, combinations of metals such as chromium, tin, yttrium, and so forth were tested to determine their suitability as promoters and stabilizers. In the examples below, except as otherwise noted, the conditions were as follows. Methyl iodide was added at a concentration of 10 wt %, and methyl acetate controlled at a concentration of 2%. Rhodium concentrations were 1000 ppm in the reactor. In each case, the balance of the reaction mixture at the start of the reaction was made up of acetic acid. Water concentrations were about 5%. The first metallic co-catalyst to rhodium molar ratio ranged from 12:1 to 20:1. A second metallic co-catalyst was used at a metal to rhodium molar ratio ranging from 0.5:1 to 10:1. The ratios provided are on a molar basis.

All the tests discussed immediately below were performed at reaction conditions of 190° C. and 30 bar total pressure. The methanol carbonylation reaction was allowed to proceed from about 2 hours to about 8 hours.

TABLE 15

Acetic acid production co-catalyzed with chromium and tin.

| Run | Rh/Cr/Sn Ratio | $H_2O$ (wt %) | Co-catalyst | Time run (hr) | STY (mol/l/hr) | Stability by visual observations |
|---|---|---|---|---|---|---|
| 15A | 1/20/1 | 5 | $CrCl_3 \cdot 6H_2O$; $SnI_4$, $SnI_2$ | 4.5 | 14 | Stable (No Rh precipitation and no solubility concerns of Cr) |

TABLE 16

Acetic acid production co-catalyzed with chromium and yttrium.

| Run | Rh/Cr/Y Ratio | $H_2O$ (wt %) | Co-catalyst | Time run (hr) | STY (mol/l/hr) | Stability by visual observations |
|---|---|---|---|---|---|---|
| 16A | 1/20/10 | 5 | $CrCl_3 \cdot 6H_2O$; $YCl_3$ | 4 | 14 | Unstable (Rh precipitation and solubility concerns of Cr/Y) |

For the experiments presented in Tables 15 and 16, when the preformation of the active Rh species in the reactor was finished (see discussion at Table 2), $SnI_4$ and $SnI_2$ or $YCl_3$ were introduced directly into the reactor (after cooling and depressurizing the reactor). The reactor was then heated and $CrCl_3 \cdot 6H_2O$ was introduced (see discussion at Table 5). At this time (with the addition of Cr salts in water), the concentration of water in the reactor was about 18%. Then the methanol carbonylation reaction began and the concentration of water decreased to 5-6% after 2 hours and this water concentration was maintained through the remainder of the experiment. During this time Rh—Cr and Rh—Sn or Rh—Y complexes were forming.

Sn stabilizes Rh and Cr, whereas Y does not. However, the combination of Cr and Sn provides low carbonylation rates when compared to Rh/Sn alone. Combinations of chromium with yttrium may be suitable in chromium amounts of 10 to 20 times the amount of rhodium present on a molar basis and in yttrium amounts of 10 to 15 times the amount of rhodium present on a molar basis.

Combinations of chromium with zinc are also believed suitable for use with water concentrations of 5 wt % or below. Suitable amounts for chromium (for example, $CrCl_3 \cdot 6H_2O$) include 10 to 20 times the amount of rhodium present on a molar basis. Suitable amounts for zinc (for example, $Zn(OAc)_2 \cdot 2H_2O$) include 0.5, 3, or 5 times the amount of rhodium present on a molar basis.

TABLE 17

Acetic acid production co-catalyzed with yttrium and zinc.

| Run | Rh/Y/Zn Ratio | $H_2O$ (wt %) | Co-catalyst | Time run (hr) | STY (mol/l/hr) | Stability by visual observations |
|---|---|---|---|---|---|---|
| 17A | 1/25/0.5 | 5 | $Y(OAc)_3 \cdot xH_2O$; $Zn(OAc)_2 \cdot 2H_2O$ | 2 | 14.6 | Unstable (solubility concerns of Y) |
| 17B | 1/20/0.5 | 5 | $Y(OAc)_3 \cdot xH_2O$; $Zn(OAc)_2 \cdot 2H_2O$ | 3.5 | 15.2 | Unstable (solubility concerns of Y) |
| 17C | 1/15/0.5 | 5 | $Y(OAc)_3 \cdot xH_2O$; $Zn(OAc)_2 \cdot 2H_2O$ | 2.6 | 16.7 | Stable (No Rh precipitation and no solubility concerns of Y) |

For experiments presented in Table 17, when the preformation of the active Rh species in the reactor was finished (see discussion at Table 2), $Y(OAc)_3$ was introduced (see discussion at Table 6). The reactor was then heated and $Zn(OAc)_2 \cdot 2H_2O$ was introduced in water solution through a feed tank into the reactor. At this time (with the addition of Y salts and Zn salts in water), the concentration of water in the reactor was about 20-15% (depending of the concentration of Y salts between 20 and 15 eq). Then the methanol carbonylation reaction began and the concentration of water decreased to 5-6% after 2 hours and this water concentration was maintained through the remainder of the experiment. During this time Rh—Y—Zn complexes as well as binary complexes were forming.

Rhodium stability was maintained at lower concentrations of yttrium, and the production rate was good. As the concentration of Y increased, solubility of Y became a concern. With a loss of rhodium stability, production rates dropped. In light of these results, suitable combinations of yttrium and zinc are believed to include yttrium in amounts of 5 to 10 times the amount of rhodium present on a molar basis and zinc in amounts of 3, 5, or 10 times the amount of rhodium present on a molar basis.

TABLE 18

Acetic acid production co-catalyzed with yttrium and tin.

| Run | Rh/Y/Sn Ratio | $H_2O$ (wt %) | Co-catalyst | Time run (hr) | STY (mol/l/hr) | Stability by visual observations |
|---|---|---|---|---|---|---|
| 18A | 1/12/0.5 | 5 | $Y(OAc)_3 \cdot xH_2O$; $SnI_4$, $SnI_2$ | 3.3 | 11 | Stable (No Rh precipitation and no solubility concerns of Y) |

For the experiment presented in Table 18, when the preformation of Rh species in the reactor was finished (see discussion at Table 2), $Y(OAc)_3$ was introduced (see discussion at Table 6) and $SnI_2+SnI_4$ were introduced (see discussion at Table 4). At this time (with the addition of Y salts and Sn salts in water), the concentration of water in the reactor was about 15%. Then the methanol carbonylation reaction began and the concentration of water decreased to 5-6% after 2 hours and this water concentration was maintained through the remainder of the experiment. During this time Rh—Y and Rh—Sn complexes were forming.

Comparing tests of rhodium catalyst systems at 5% water for Rh/LiI at a 1/15 molar ratio with Rh/Y/Sn at a 1/20/0.5 molar ratio, it appears that Sn stabilizes Rh better than LiI at a lower metal to rhodium molar ratio. Rh/Y/Sn provides carbonylation rates similar to Rh/LiI at a 1/15 molar ratio. Comparing tests of rhodium catalyst systems at 5% water for Rh/Sn at a 1/0.5 molar ratio with Rh/Y/Sn at a 1/20/0.5 molar ratio, the results show that tin stabilizes rhodium in both systems and appears to stabilize yttrium as well, but the yttrium/tin combination provides lower production rates than does tin alone.

TABLE 19

Acetic acid production co-catalyzed with yttrium and HPA.

| Run | Rh/Y/HPA Ratio | $H_2O$ (wt %) | Co-catalyst | Time run (hr) | STY (mol/l/hr) | Stability by visual observations |
|---|---|---|---|---|---|---|
| 19A | 1/15/5 | 5 | $Y(OAc)_3 \cdot xH_2O$; $H_3PW_{12}O_{40} \cdot xH_2O$ | 3 | 10.6 | Stable (No Rh precipitation and no solubility concerns of Y) |

For the experiment presented in Table 19, when the preformation of Rh species in the reactor was finished (see discussion at Table 2), $Y(OAc)_3$ was introduced (see discussion at Table 6) and HPA was introduced in the flasher medium before this material was recycled to the reactor during the beginning of the experiment and prior to methanol carbonylation. At this time (with the addition of Y salts in water), the concentration of water in the reactor was about 15%. Then the methanol carbonylation reaction began and the concentration of water decreased (to 5-6%) after 2 hours and this water concentration was maintained through the remainder of the experiment. During this time Rh—Y-HPA complexes were forming.

The Rh/Y/HPA combination provided similar results to that of the Rh/Y/Sn combination.

In summary, yttrium in combination with zinc, tin, and an HPA provided catalyst stability. Yttrium in combination with zinc also provided STYs above 12, as did chromium in combination with tin. Chromium in combination with yttrium and aluminum in combination with indium provided an STY above 12, but did not provide catalyst stability.

Combinations of yttrium with ruthenium and yttrium with bismuth are also believed suitable for use with water concentrations of 5 wt % or below. Suitable amounts for yttrium include 5 to 10 times the amount of rhodium present on a molar basis. Suitable amounts for ruthenium (for example, $RuI_3$) or bismuth (for example, $Bi(OAc)_3$) include 1, 5, or 10 times the amount of rhodium present on a molar basis.

Examples 20-24

End-run Analyses

To demonstrate that selected co-catalyst metals contribute substantially less than equivalent amounts of inorganic iodide to a carbonylation system at equilibrium, a series of runs were performed under continuous conditions. For comparison, a run co-catalyzed with lithium iodide was performed as described generally above. In addition, runs were performed using chromium, lanthanum, and a binary metal combination of yttrium and zinc. A batch run co-catalyzed with chromium was also performed. Following generally the procedures noted above, combinations of metals such as chromium, tin, yttrium, and so forth were tested to determine their suitability as promoters and stabilizers. In the continuous examples below, except as otherwise noted, the conditions were as follows. Methyl iodide was added at a concentration of 10 wt %, and methyl acetate controlled at a concentration of 2%. Rhodium concentrations were 1000 ppm in the reactor. Water concentrations were about 5%. In each case, the balance of the reaction mixture at the start of the reaction was made up of acetic acid.

All the tests discussed below were performed at reaction conditions of 190° C. and 30 bar total pressure. The methanol carbonylation reaction was allowed to proceed from about 2 hours to about 8 hours. The conditions and results are summarized in Tables 20 and 21, below. The ratios provided are on a molar basis. Table 20 provides data comparable to the data provided in the previous examples. Table 21 provides additional information not available for the previous examples.

The runs for Examples 20A-20E were performed using essentially the same procedure as was used for the previous examples. For instance, for run 20B, $Cr(OAc)_3$ was introduced either in water solution through a feed tank into the reactor, or as a solid directly into the reactor, after the preformation of the active Rh species in the reactor at the beginning of the reaction. At this time, the concentration of water in the reactor was about 10%. Then the methanol carbonylation reaction began and the concentration of water decreased to 5-6% after 2 hours and this water concentration was maintained through the remainder of the experiment. During this time the inorganic iodide concentration was less than about 0.8 wt %, which indicates that at the high Cr concentration, the form of the Cr salt present was not as an iodide salt.

TABLE 20

Acetic acid production co-catalyzed with metallic co-catalysts.

| Run | Rh/Metal Ratio | $H_2O$ (wt %) | Co-catalyst | Time run (hr) | STY (mol/l/hr) | Stability by visual observations |
|---|---|---|---|---|---|---|
| 20A | 1/76 | 5 | LiI | 4 | 18 | Stable |
| 20B | 1/20 | 5 | $Cr(OAc)_3$ | 5 | 18 | Stable |
| 20C | 1/30 | 5 | $LaCl_3$ | 6 | 14 | Stable |
| 20D | 1/15/0.5 | 5 | $Y(OAc)_3 \cdot xH_2O$; $Zn(OAc)_2 \cdot 2H_2O$ | 5 | 16 | Stable |
| 20E (Batch) | 1/20 | 5 | $Cr(OAc)_3$ | 0.17 | 14 | Stable |

Note that all of the co-catalytic transition metal runs presented in Table 20 achieved production rates comparable to the lithium iodide run and provided rhodium stability to the system. A sample of the reaction mixture from each run was titrated for halide (e.g., iodide) content. Corrosion metal content and resultant impurities were also determined. The quantity of corrosion metals is a function of corrosion of the reactor material. The amount varies depending on a variety of factors: run time, temperature, catalysts used and the pre-existing corrosion level of the reactor. Thus, it is difficult to compare corrosion metal amounts between runs, or to compare corrosion metal amounts from one system to another. The results are shown below.

Theoretically equivalent inorganic iodide content was calculated as follows. Iodine has a molecular weight of 126.904 g/mol. The theoretical mass of inorganic iodide was calculated by multiplying the molar ratio of metal to rhodium by the valence of the metal and the molecular weight of iodine. The mass of inorganic iodide was divided by the total mass of the reaction mixture and multiplied by 100 to achieve a theoretical weight percent inorganic iodide content. For example, given a rhodium concentration of 1000 ppm, a lanthanum form of $LaCl_3$ (i.e., valence of 3), and a lanthanum:rhodium molar ratio of 30:1, the theoretical inorganic iodide content in Run 20C (Lanthanum) was calculated as follows.

Mass of inorganic iodide:
30 mol×valence 3×126.904 g/mol=11421.4 g (based on one mol of Rh)

Total reaction mixture mass (based on one mol of Rh):
Rh: 102.905 g
Total mass: 1000×mass of Rh: 1000×102.905 g=102905 g
Theoretical inorganic iodide content:
(11421.4 g/102905 g)×100=11.0989%

Alternatively, given the mass of lanthanum in weight %, the theoretical iodide content may be found by multiplying the mass of lanthanum by the valence and a ratio of the molecular weight of iodine to the molecular weight of chromium. In systems where two metal compositions were added, a theoretical inorganic iodide value was similarly calculated for the second metal present in the system, and the theoretical values of iodide from the first and second metal compositions were added. Note that the calculations provided herein use the valence of the form of each metallic co-catalyst as it was introduced. An alternate valence would only be used if it was otherwise clear that the valence of the metal changes after introduction to the system.

The actual iodide content in the system was determined by titration as described above. Note that entries labeled "ND" indicate that the impurity was not detected. The detection limit for the analytical method used herein is 10 ppm.

stability, but contribute a significantly lower inorganic iodide concentration to the reaction mixture. Further, the impurity profile, i.e., the relative amounts of each impurity, is profoundly affected by the metal in each run. When the inorganic iodide of the system is low, such impurities are dramatically reduced. Iodide levels below about 1 weight % reduced acetaldehyde levels by about 48%, and propionic acid levels by about 78%, compared to the lithium iodide system results.

Additional experiments performed for Rh, Rh/Ni, Rh/Zr, Rh/Fe, Rh/Mo, Rh/In, and Rh/W were performed using a 5 wt % water concentration. No significant difference in activity or stability was noted in comparison to previously discussed experiments using a 6 wt % water concentration.

To further demonstrate that selected co-catalyst metals contribute substantially less than equivalent amounts of inorganic iodide to a carbonylation system at equilibrium, an additional series of runs were performed under continuous conditions. For comparison, a run co-catalyzed with lithium iodide was performed as described generally above. In addition, runs were performed using a variety of metals and binary metal combinations. In the examples below, methyl iodide was added at a concentration of 10 wt %, and methyl acetate controlled at a concentration of 2%. Rhodium concentrations were 1000 ppm in the reactor. Water concentrations were about 5%. In each case, the balance of the reaction mixture at the start of the reaction was made up of acetic acid. The ratios provided are on a molar basis.

All the tests discussed below were performed at reaction conditions of 190° C. and 30 bar total pressure. The methanol carbonylation reaction was allowed to proceed from about 1.5

TABLE 21

Iodide concentration, end-run conditions, corrosion metal analyses and impurities formation for various co-catalysts.

| Run | Co-catalyst Concentration (wt %) | Theoretical Iodide Content (wt %; calculated) | Iodide titration results (wt %) | End Run conditions H₂O (wt %) | AcOMe (wt %) | MeI (wt %) | Corrosion Metals, ppm Fe | Ni | Mo | Impurities, ppm Acetaldehyde | Crotonaldehyde | Ethyl-crotonaldehyde | Propionic Acid |
|---|---|---|---|---|---|---|---|---|---|---|---|---|---|
| 20A | Li: 0.5 | 9.1 | 9 | 5 | 1.9 | 8.5 | 20 | 186 | 163 | 457 | ND | ND | 166 |
| 20B | Cr: 1 | 7.3 | 0.7 | 4 | 2 | 11 | 20 | 63 | 121 | 171 | 15 | ND | 21 |
| 20C | La: 4 | 11 | 2.1 | 5 | 2 | 10 | 57 | 760 | 332 | 443 | 23 | ND | 26 |
| 20D | Y: 1.3; Zn: 0.03 | 5.7 | 2.8 | 7 | 11 | 13 | 760 | 114 | 195 | 265 | 21 | ND | 107 |
| 20E (batch) | Cr: 1 | 7.3 | 0.3 | 1.7 | 17 | 7.3 | 5 | 41 | 28 | N/A | N/A | N/A | N/A |

Without intending to be bound by theory, the propionic acid levels are believed to be more representative of the impurity profile achieved by each composition than is acetaldehyde. Acetaldehyde has a boiling point of about 20.2° C., in contrast to propionic acid which has a boiling point of about 140.7° C. Acetaldehyde and propionic acid flash off with the product acetic acid (B.P. 118° C.) and are condensed. A fraction of the acetaldehyde may be lost as the condensed mixture is removed from the condenser as well as during analysis of the impurities.

The results in Table 21 show that metallic co-catalyst compositions including metals such as chromium and lanthanum and binary metal co-catalyst compositions such as yttrium and zinc achieve comparable results to a rhodium/lithium iodide carbonylation system in terms of STY and catalyst hours to about 8 hours. The conditions and results are summarized in Tables 22 and 23, below. Table 22 provides data comparable to the data provided in the previous examples. Table 23 provides additional information similar to Table 21.

The runs for Examples 22A-22O were performed using essentially the same procedure as was used for the previous examples. For instance, for run 22E, $Cr(OAc)_3$ and $RuI_3$ were introduced directly into the reactor after the preformation of the active Rh species in the reactor at the beginning of the reaction. At this time, the concentration of water in the reactor was about 10%. Then the methanol carbonylation reaction began and the concentration of water decreased to 5-6% after 2 hours and this water concentration was maintained through the remainder of the experiment. During this time the inorganic iodide concentration was less than about 1.1 wt %, which indicates that at the high Cr and Ru concentrations, the forms of the Cr and salts present were not as iodide salts.

Figure 4:
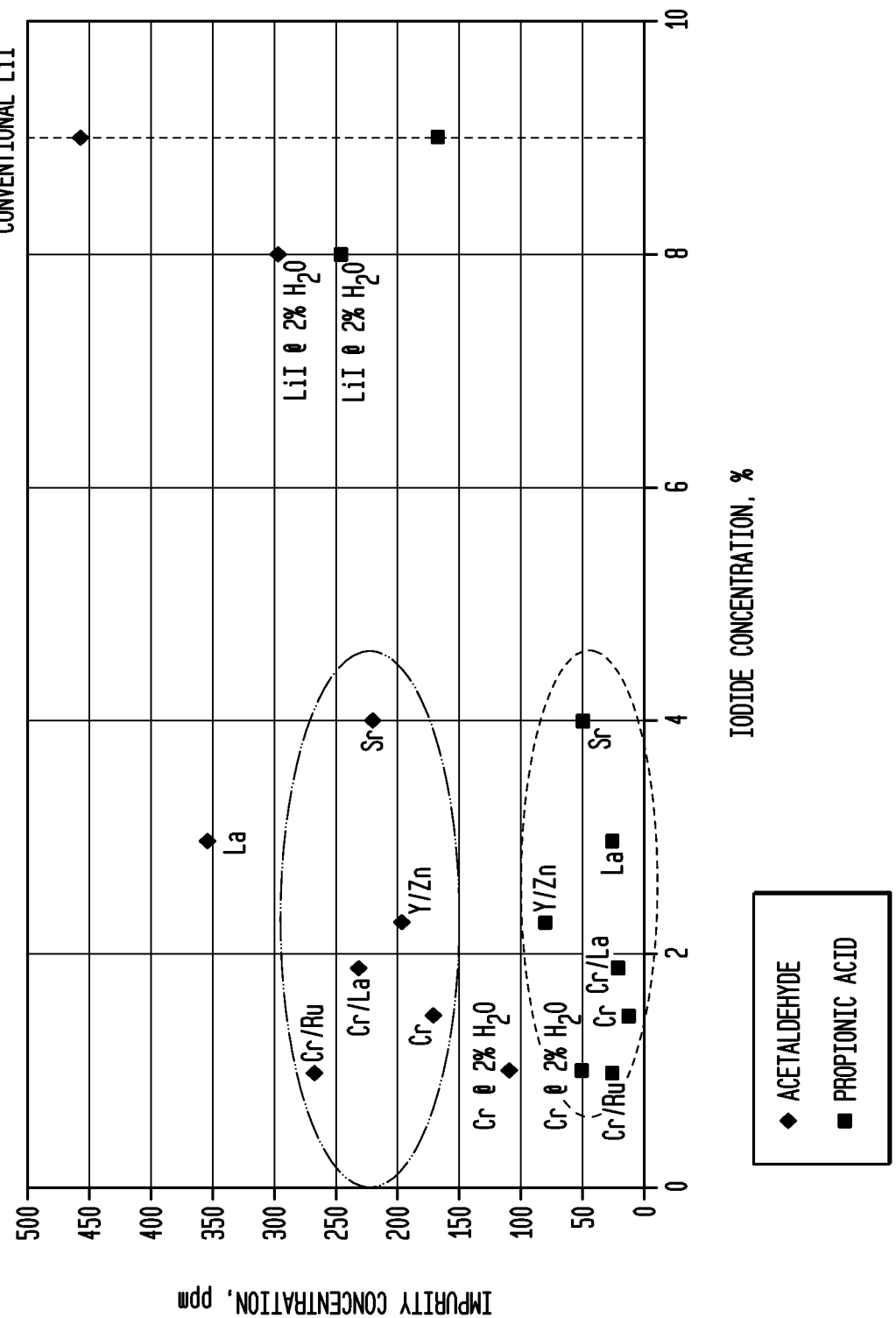
FIG. 4 is a graphical depiction of impurities produced during carbonylation (at 5 wt % water except as noted) using metal compositions according to the invention in comparison to conventional lithium iodide as a function of iodide concentration.

Runs that provided unstable systems were not analyzed further. Therefore, no data is provided in Table 23 for unstable cocatalyst combinations and molar ratios, with the exception of lithium iodide at a molar ratio to rhodium of 38:1 and end-run conditions for vanadium, barium, and bismuth. Note that Tables 22-25 are the sources of data for FIGS. 4 and 5. FIG. 4 demonstrates the lowered impurity concentrations, as a function of iodide concentration, resulting from use of metallic co-catalysts according to the invention as compared to a conventional lithium iodide system. Similarly, FIG. 5 demonstrates impurity concentrations as a function of STY. The systems were operated at 5 wt % water, except where noted.

Make rates for impurities produced in a system according to the invention may be calculated by multiplying the impurity concentration (ppm) in the acetic acid product by the carbonylation rate, or STY (mol/L/hr), multiplied by the molecular weight of acetic acid (60.05196 g/mol), divided by the molecular weight of the impurity, resulting in a rate of moles impurity per liter per hour (x $10^{-6}$). For propionic acid, the molecular weight is 74.07854 g/mol; for acetaldehyde, the molecular weight is 44.05256. The metallic co-catalysts according to the invention have been shown to achieve propionic acid make rates about 40% to about 93% lower than a conventional lithium iodide-stabilized system, and acetaldehyde make rates about 25% to about 99% lower than a conventional system.

The following experiments demonstrate the applicability of the invention to systems operated at very low water levels. Chromium and lithium iodide were tested, generally following the procedures noted above. In the examples below, methyl iodide was added at a concentration of 10 wt %, and methyl acetate controlled at a concentration of 2%. Rhodium concentrations were 1000 ppm in the reactor. Water concentrations were about 2%. The ratios provided are on a molar basis.

All the tests discussed below were performed at reaction conditions of 190° C. and 30 bar total pressure. The methanol carbonylation reaction was allowed to proceed for about 4 hours.

TABLE 22

Acetic acid production co-catalyzed with metallic co-catalysts.

| Run | Rh/Metal Ratio | Co-catalyst | $H_2O$ (wt %) | Time run (hr) | STY (mol/l/hr) | Stability by visual observations |
|---|---|---|---|---|---|---|
| 22A | 1/76 | LiI | 5 | 4 | 18 | Stable |
| 22B | 1/15/0.5 | Y(OAc)$_3$; Zn(OAc)$_2$ | 5 | 3 | 16 | Stable |
| 22C | 1/15 | Sr(OAc)$_2$ | 5 | 4 | 15.5 | Stable |
| 22D | 1/30 | LaCl3 | 5 | 4 | 15 | Stable |
| 22E | 1/20/3 | Cr(OAc)$_3$; RuI$_3$ | 5 | 8 | 16.5 | Stable |
| 22F | 1/20/5 | Cr(OAc)$_3$; LaCl$_3$•H$_2$O | 5 | 7 | 17.1 | Stable |
| 22G | 1/20 | Cr(OAc)$_3$ | 5 | 4 | 17 | Stable |
| 22H | 1/15 | Mn(OAc)$_3$ | 5 | 1.5 | 9 | Stable |
| 22I | 1/38 | LiI | 5 | 4 | 16.5 | Unstable |
| 22J | 1/20/10 | CrCl$_3$•6H$_2$O; YCl$_3$ | 5 | 4 | 14 | Unstable |
| 22K | 1/15/1 | AlI$_3$; InI$_3$ | 5 | 3 | 14 | Unstable |
| 22L | 1/15 | Ba(OAc)$_2$ | 5 | 2.5 | 14 | Unstable |
| 22M | 1/30 | Ba(OAc)$_2$ | 5 | 1.5 | 13 | Unstable |
| 22N | 1/10 | VCl$_3$ | 5 | 3 | 12 | Unstable |
| 22O | 1/15 | Bi(OAc)$_3$ | 5 | N/A | N/A | Unstable |

TABLE 24

Acetic acid production co-catalyzed with metallic co-catalysts.

| Run | Rh/Metal Ratio | Co-catalyst | $H_2O$ (wt %) | Time run (hr) | STY (mol/l/hr) | Stability by visual observations |
|---|---|---|---|---|---|---|
| 24A | 1/76 | LiI | 2 | 4 | 16.5 | Stable |
| 24B | 1/20 | Cr(OAc)$_3$ | 2 | 4 | 15 | Stable |

TABLE 23

Iodide concentration, end-run conditions, and impurities formation for various co-catalysts.

| Run | Co-catalyst Concentration (wt %) | Theoretical Iodide Content (wt %; calculated) | Iodide titration results (wt %) | End Run conditions | | | Impurities, ppm | | | |
| | | | | $H_2O$ (wt %) | AcOMe (wt %) | MeI (wt %) | Acetaldehyde | Crotonaldehyde | Ethylcrotonaldehyde | Propionic Acid |
|---|---|---|---|---|---|---|---|---|---|---|
| 22A | Li: 0.5 | 9.1 | 9 | 5 | 1.9 | 8.5 | 457 | ND | ND | 166 |
| 22B | Y: 1.3; Zn: 0.03 | 5.7 | 2.3 | 5 | 3 | 10 | 197 | ND | ND | 80 |
| 22C | Sr: 1.3 | 3.6 | 4.4[1] | 5 | 3.5 | 15 | 220 | ND | ND | 49 |
| 22D | La: 4 | 11 | 3 | 6 | 7 | 10 | 353 | ND | ND | 26 |
| 22E | Cr: 1; Ru: 0.3 | 8.4 | 1 | 4 | 3 | 9 | 267 | ND | ND | 25 |
| 22F | Cr: 1; La: 0.7 | 9.2 | 1.9 | 4 | 2 | 9 | 231 | ND | ND | 21 |
| 22G | Cr: 1 | 7.3 | 1.5 | 4 | 3 | 10 | 1711 | ND | ND | 12 |
| 22H | Mn: 0.8 | 5.5 | 6.5[1] | 11.7 | 25 | 14 | 204 | ND | ND | 0 |
| 22I | Li: 0.25 | 4.6 | 5[1] | 5 | 4 | 16 | 256 | ND | ND | 52 |
| 22L | Ba: 1.9 | 3.6 | N/A | 9.5 | 15 | 12 | N/A | N/A | N/A | N/A |
| 22M | Ba: 3.8 | 7.2 | N/A | 8 | 10 | 11 | N/A | N/A | N/A | N/A |
| 22N | V: 0.5 | 3.7 | 2.3 | 12 | 25 | 14 | N/A | N/A | N/A | N/A |
| 22O | Bi: 3 | 5.5 | N/A | N/A | N/A | N/A | N/A | N/A | N/A | N/A |

[1]Difference between theoretical and experimental iodide results is believed due to experimental error; For purposes of analysis, the iodide value of Sr (Run 22C) has been rounded to 4, the iodide value of Mn (Run 22H) has been rounded to 6, and the iodide value of Li (Run 22I) has been rounded to 5.

TABLE 25

Iodide concentration, end-run conditions, and impurities formation for various co-catalysts.

| Run | Co-catalyst Concentration (wt %) | Theoretical Iodide Content (wt %; calculated) | Iodide titration results (wt %) | End Run conditions | | | Impurities, ppm | | | |
|---|---|---|---|---|---|---|---|---|---|---|
| | | | | $H_2O$ (wt %) | AcOMe (wt %) | MeI (wt %) | Acetaldehyde | Crotonaldehyde | Ethyl-crotonaldehyde | Propionic Acid |
| 24A | Li: 0.5 | 9.1 | 8 | 2.1 | 2.5 | 9.1 | 297 | ND | ND | 246 |
| 24B | Cr: 1 | 7.3 | 1 | 3.0 | 6.0 | 10.0 | 110 | ND | ND | 51 |

Runs 24A and 24B demonstrate that the method according to the invention can be successfully performed at low water concentrations. Without being bound by theory, it is believed that the level of acetaldehyde decreases with decreasing water concentration because there is less hydrogen available in the reaction medium.

Other suitable combinations for use in systems having a water concentration of 5 wt % or less are listed in Table 26. Run conditions include: 2 wt % methyl acetate; 10 wt % methyl iodide; and a concentration of rhodium in the reactor of 1000 ppm. In each case, the balance of the reaction mixture at the start of the reaction is made up of acetic acid.

TABLE 26

Acetic Acid Production Co-catalyzed with various co-catalysts.

| Run | Rh/Metal 1/Metal 2 Ratio | Co-catalyst(s) |
|---|---|---|
| 26A | 1/15/3 | Cr/Ru |
| 26B | 1/5/0 | V |
| 26C | 1/25/3 | Al/Ru |
| 26D | 1/5/0.5 | Al/Sn |
| 26E | 1/15/0.5 | Ba/Sn |
| 26F | 1/25/0.5 | Be/Sn |
| 26G | 1/15/3 | Co/Ru |
| 26H | 1/25/0.5 | Co/Zn |
| 26I | 1/25/1 | Co/In |
| 26J | 1/25/0.5 | Co/Sn |
| 26K | 1/5/0.5 | Cr/Zn |
| 26L | 1/15/1 | Cr/In |
| 26M | 1/5/5 | Cr/HPA |
| 26N | 1/25/5 | La/Cu |
| 26O | 1/25/0.5 | Mn/Sn |
| 26P | 1/15/5 | Mo/HPA |
| 26Q | 1/15/3 | Sr/Ru |
| 26R | 1/25/0.5 | Sr/Zn |
| 26S | 1/15/0.5 | Sr/Sn |
| 26T | 1/25/5 | Sr/HPA |
| 26U | 1/15/0.5 | V/Sn |
| 26V | 1/25/0.5 | V/Zn |
| 26W | 1/25/5 | V/HPA |
| 26X | 1/15/1 | V/In |
| 26Y | 1/15/3 | V/Ru |
| 26Z | 1/15/25 | Y/La |
| 26AA | 1/25/15 | Y/Ru |
| 26AB | 1/25/0.5 | Y/In |
| 26AC | 1/5/15 | Y/Co |

While the metals exemplified above are preferred, other metals may also be used, as discussed below. As a result primarily of the experimentation described above, lithium, potassium, zinc, ruthenium, manganese, heteropoly acids, indium, and tin are considered to be primarily stabilizers. Vanadium, barium, and yttrium are considered to be primarily activators. Chromium, nickel, strontium, and lanthanum are considered to be both activators and stabilizers. Beryllium, hafnium, cobalt, copper and platinum may be successful activators or stabilizers. Several metals showed promising results during testing, but were introduced in a form that did not achieve adequate solubility. A soluble form of these metals may also provide activation and/or stabilization. These metals include aluminum, titanium, iron, zirconium, molybdenum, tungsten, and bismuth.

There is thus provided in a first aspect of the invention, a continuous process for the production of acetic acid. In the process, a compound selected from the group consisting of methanol and reactive derivatives thereof is reacted with carbon monoxide to produce acetic acid in an aqueous reaction mixture. During the reaction, a concentration of water of from 0.1 wt % up to about 8 wt % is maintained in the reaction mixture. The reaction is carried out in the presence of a homogeneous rhodium-based catalyst system comprising a rhodium catalyst metal; an iodide promoter; and a metallic co-catalyst composition including a metal selected from the group consisting of transition metals, zinc, beryllium, indium, tin, strontium, barium, and mixtures thereof, and optionally further including a heteropoly acid (HPA). Acetic acid is recovered from the reaction mixture. The process is controlled and the metallic co-catalyst composition is selected so that it is effective as a stabilizer and a rate promoter, and the reaction mixture contains substantially less than a theoretically equivalent inorganic iodide content corresponding to the presence of the metallic co-catalyst composition.

The reaction mixture according to the invention contains substantially less than the theoretically equivalent inorganic iodide content, including inorganic iodide, corresponding to the presence of the metallic co-catalyst composition. Generally, the amount of inorganic iodide present is less than 60% of the theoretically equivalent inorganic iodide content corresponding to the presence of the metallic co-catalyst composition. Typically, the amount of inorganic iodide present is less than 50%, preferably less than 40%, more preferably less than 30%, even more preferably less than 20%, and most preferably less than 10% of the theoretically equivalent inorganic iodide content corresponding to the presence of the metallic co-catalyst composition.

The process is generally operated with an inorganic iodide content in the reaction mixture of less than 3.5 weight %. Typically, the process is operated with an inorganic iodide content in the reaction mixture of less than 3 weight %, preferably less than 2 weight %, and more preferably, less than 1 weight %.

Generally, the amount of inorganic iodide present is less than 60% of the theoretically equivalent inorganic iodide content corresponding to the presence of the metallic co-catalyst composition and the inorganic iodide content in the reaction mixture is less than 3.5 weight %. Typically, the amount of inorganic iodide present is less than 50% of the theoretically equivalent inorganic iodide content corresponding to the presence of the metallic co-catalyst composition and the inorganic iodide content in the reaction mixture is less than 3 weight %. Preferably, the amount of inorganic iodide present is less than 50% of the theoretically equivalent inorganic iodide content corresponding to the presence of the metallic co-catalyst composition and the inorganic iodide content in the reaction mixture is less than 2 weight %. More preferably, the amount of inorganic iodide present is less than 50% of the theoretically equivalent inorganic iodide content corresponding to the presence of the metallic co-catalyst composition and the inorganic iodide content in the reaction mixture is less than 1 weight %.

The method is characterized by a reaction productivity (STY) greater than 10 moles/L/hr. The iodide promoter is typically methyl iodide.

Generally, the metallic co-catalyst composition maintains stability of the rhodium catalyst metal in water concentrations of less than 7 weight %. Thus, the water content of the reaction mixture is generally maintained at less than 7 weight %. Typically, the water content of the reaction mixture is maintained at a level of from 1 weight % to 7 weight %. In some aspects of the invention, the water content of the reaction mixture is maintained at a level of from 2 weight % to 6 weight % or from 0.2 weight % to 5 weight %, such as from 3 weight % to 5 weight %. Preferably, the water content of the reaction mixture is maintained at 3 weight % or less, such as from 0.5 weight % to 3 weight %, from 1 weight % to 2.75 weight %, or from 1.5 weight % to 2.5 weight %. In some cases the amount of water in the reaction mixture is generally maintained from about 0.1 weight percent up to less than 8 weight percent, and in some cases up to 10% by weight of the reaction mixture.

The process is generally operated with a total inorganic iodide content in the reaction mixture of less than 4 weight % and the water content of the reaction mixture is maintained at a level of less than 5 weight %. Typically, the total inorganic iodide content in the reaction mixture of less than 3.5 weight %, preferably less than 3 weight %, more preferably less than 2.5 weight %, for example less than 2 weight % or less than 1.5 weight %, and the water content of the reaction mixture is maintained at a level of less than 5 weight %, such as from 0.5 to less than 5 weight %.

The molar ratio of metal/rhodium in the reaction mixture is suitably at least 0.5/1 in many implementations of the inventive process.

In some embodiments, the metallic co-catalyst composition comprises a single metal compound. The single metal compound comprises a metal selected from tin, present in a tin:rhodium molar ratio of less than 10:1, such as less than 1:1; chromium present in a chromium:rhodium molar ratio of at least 5:1 and up to 30:1; beryllium present in a metal:rhodium molar ratio of at least 5:1 and up to 30:1; zinc present in a zinc:rhodium molar ratio of at least 0.5:1 and up to 10:1; and beryllium, hafnium, cobalt, platinum, copper, strontium or lanthanum in a metal:rhodium molar ratio of at least 0.5:1 and less than 40:1.

In other embodiments, the metallic co-catalyst composition comprises two metal compounds. In these embodiments, the two metal compounds comprise metal combinations selected from chromium and tin; chromium and zinc; yttrium and a stabilizing component; vanadium and a stabilizing component; and barium and a stabilizing component. In embodiments having a chromium component, chromium is generally present in a chromium:rhodium molar ratio of at least 5:1, up to a molar ratio of 30:1 and tin or zinc is generally present in a tin or zinc:rhodium molar ratio of 10:1 or less. In embodiments having an yttrium component, yttrium is generally present in an yttrium:rhodium molar ratio of at least 5:1 and less than 20:1 and the stabilizing component is generally present in a metal:rhodium molar ratio of at least 0.5:1 and less than 20:1. Suitable stabilizing components for yttrium comprise a metal chosen from the group consisting of tin, manganese, ruthenium, zinc and indium. In embodiments having a vanadium component, vanadium is generally present in a vanadium:rhodium molar ratio of at least 5:1 and less than 20:1. Suitable stabilizing components for vanadium comprise a metal chosen from the group consisting of chromium, nickel, tin, zinc, ruthenium, manganese, indium, and a heteropoly acid. In embodiments having a barium component, barium is generally present in a barium:rhodium molar ratio of at least 5:1 and less than 20:1. Suitable stabilizing components for barium comprise a metal chosen from the group consisting of tin, zinc, ruthenium, manganese, indium, and a heteropoly acid.

Generally, the reaction mixture contains from 250 ppm rhodium to 3000 ppm rhodium, such as from 500 ppm rhodium to 2000 ppm rhodium. Preferably, the metallic co-catalyst composition is added to the reaction mixture in the +1, +2, +3, +4, +5 or +6 oxidation state.

A particularly useful commercial embodiment is a continuous process for the production of acetic acid in an aqueous reaction mixture comprising reacting a compound, selected from the group consisting of methanol and reactive derivatives thereof, with carbon monoxide in a pressurized reactor at elevated pressure. There is maintained in the reaction mixture during the course of the reaction: (i) a homogeneous rhodium catalyst metal; (ii) from about 1 to about 20 weight percent methyl iodide; and (iii) a metallic co-catalyst composition selected so that the metallic co-catalyst composition is effective as a stabilizer and a rate promoter. The metallic co-catalyst composition includes one or more metals selected from the group consisting of transition metals, zinc, beryllium, indium, tin, strontium, barium, and mixtures thereof, and optionally further including heteropoly acids (HPA). The reaction mixture contains substantially less than a theoretically equivalent inorganic iodide content corresponding to the presence of the metallic co-catalyst composition. The reaction mixture maintains a water concentration of from 0.1 weight percent up to less than 8 weight percent and a methyl acetate concentration about 0.5 to about 30 weight percent. Acetic acid is also present. The reaction mixture is provided in a stream of to a flash vessel at a reduced pressure, where crude acetic acid product is flashed from the reaction mixture. Generally, the crude product stream includes acetic acid as well as significant levels of methyl acetate, methyl iodide and water. the crude product stream is sent to a light ends column where it is purified to remove methyl acetate and methyl iodide. Thereafter, a partially purified product, that is, purified of light ends, is sent to a dehydration column where water is removed therefrom. In some cases the amount of water in the reaction mixture is generally maintained from about 0.1 weight percent up to less than 8 weight percent, and in some cases up to 10% by weight of the reaction mixture.

A preferred alternate embodiment is one in which the a metallic co-catalyst composition includes a metal selected from the group consisting of chromium and lanthanum and mixtures thereof, and optionally further including a heteropoly acid (HPA).

Lower aldehyde generation can reduce or eliminate the need for aldehyde removal, which can be expensive. See, for example U.S. patent application Ser. No. 11/116,771 (Publication No. US 2006/0247466) of Zinobile et al., the disclosure of which is incorporated herein by reference.

Generally, the amount of inorganic iodide present is less than 50 percent of the theoretically equivalent inorganic iodide content corresponding to the presence of the metallic co-catalyst composition as noted above. So also, in most cases, the process is operated with an inorganic iodide content in the reaction mixture of less than 3.5 weight % such as less than 3 weight % or less than 2 weight % or even less than 1 weight %. These features are independently combined, for example, as noted below.

The process is generally carried out wherein the amount of inorganic iodide present is less than 50% of the theoretically equivalent inorganic iodide content corresponding to the presence of the metallic co-catalyst composition and the inorganic iodide content in the reaction mixture is less than 3.5 weight % such as wherein the amount of inorganic iodide present is less than 50% of the theoretically equivalent inorganic iodide content corresponding to the presence of the metallic co-catalyst composition and the inorganic iodide content in the reaction mixture is less than 2 weight % or wherein the amount of inorganic iodide present is less than 50% of the theoretically equivalent inorganic iodide content corresponding to the presence of the metallic co-catalyst composition and the inorganic iodide content in the reaction mixture is less than 1 weight %.

The process is sometimes characterized by a propionic acid concentration of less than 90 parts per million as measured at the flash vessel overhead such as when characterized by a propionic acid concentration of less than 60 parts per million as measured at the flash vessel overhead or less than 30 parts per million as measured at the flash vessel overhead. In preferred cases the process is characterized by a propionic acid concentration of less than 25 parts per million as measured at the flash vessel overhead and a partial pressure of carbon monoxide is maintained above 1 bar in the pressurized reactor. In some cases, the partial pressure of carbon monoxide is maintained below 1 bar in the flash vessel.

In another embodiment, there is provided a continuous process for the production of acetic acid comprising: (a) reacting a compound, selected from the group consisting of methanol and reactive derivatives thereof, with carbon monoxide to produce acetic acid in an aqueous reaction mixture, the reaction being carried out while maintaining a concentration of water in the reaction mixture of from 0.1 wt % up to about 5 wt %, the reaction also being carried out in the presence of a homogeneous rhodium-based catalyst system comprising: (i) a rhodium catalyst metal; (ii) an iodide promoter; and (iii) a metallic co-catalyst composition including a metal selected from the group consisting of transition metals, zinc, beryllium, indium, tin, strontium, barium, and mixtures thereof, and optionally further including a heteropoly acid (HPA) in a metal to rhodium molar ratio of at least 0.5:1 and up to 20:1; and (b) recovering acetic acid from the reaction mixture, wherein the process is controlled and the metallic co-catalyst composition is selected so that it is effective as a stabilizer and a rate promoter.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. A continuous process for the production of acetic acid comprising:
   (a) reacting a compound, selected from the group consisting of methanol and reactive derivatives thereof, with carbon monoxide to produce acetic acid in an aqueous reaction mixture, the reaction being carried out while maintaining a concentration of water in the reaction mixture of from 0.1 wt % up to about 8 wt %, the reaction also being carried out in the presence of a homogeneous rhodium-based catalyst system comprising:
      (i) a rhodium catalyst metal;
      (ii) an iodide promoter; and
      (iii) a metallic co-catalyst composition including a metal selected from the group consisting of titanium, vanadium, chromium, manganese, iron, cobalt, nickel, copper, yttrium, zirconium, molybdenum, ruthenium, lanthanum, hafnium, tungsten, platinum, zinc, beryllium, indium, tin, strontium, barium, and mixtures thereof, and optionally further including a heteropoly acid (HPA); and
   (b) recovering acetic acid from the reaction mixture;
   wherein the process is controlled and the metallic co-catalyst composition is selected so that it is effective as a stabilizer and a rate promoter, and the reaction mixture contains substantially less than a theoretically equivalent inorganic iodide content corresponding to the presence of the metallic co-catalyst composition.

2. The process according to claim 1, wherein the amount of inorganic iodide present is less than 60% of the theoretically equivalent inorganic iodide content corresponding to the presence of the metallic co-catalyst composition.

3. The process according to claim 1, wherein the process is operated with an inorganic iodide content in the reaction mixture of less than 3.5 weight %.

4. The process according to claim 1, wherein the process is further characterized by a reaction productivity (STY) greater than 10 moles/L/hr.

5. The process according to claim 1, wherein the iodide promoter is methyl iodide maintained in said reaction mixture in a concentration of from about 1 to about 20 weight percent.

6. The process according to claim 1, wherein the process is operated with a total inorganic iodide content in the reaction mixture of less than 4 weight % and the water content of the reaction mixture is maintained at a level of less than 5 weight %.

7. The process according to claim 1, wherein the metallic co-catalyst composition comprises a single metal compound.

8. The process according to claim 1, wherein the metallic co-catalyst composition comprises two metal compounds.

9. The process according to claim 1, wherein the reaction mixture contains from 250 ppm rhodium to 3000 ppm rhodium.

10. The process according to claim 1, wherein the aqueous reaction mixture is disposed in a pressurized reactor at elevated pressure of at least 10 bar,
    and wherein the homogeneous rhodium-based aqueous catalyst system further comprises
    (iv) methyl acetate maintained in said reaction mixture in a concentration of from about 0.5 to about 30 weight percent; and
    (v) acetic acid;
    wherein further the step of recovering acetic acid comprises
    providing a stream of the reaction mixture to a flash vessel at a reduced pressure of less than 3 bar;
    flashing crude acetic acid product from the reaction mixture to generate a crude product stream including acetic acid, methyl acetate, methyl iodide and water; and
    purifying the crude product stream to remove methyl acetate, methyl iodide and water therefrom, to obtain a purified acetic acid product.

11. The process according to claim 10, wherein the process is further characterized by a propionic acid concentration of less than 90 parts per million as measured at the flash vessel overhead.

12. The process according to claim 10, wherein a partial pressure of carbon monoxide is maintained above 1 bar in the pressurized reactor.

13. The process according to claim 10, wherein a partial pressure of carbon monoxide is maintained below 1 bar in the flash vessel.

14. The process according to claim 1, wherein:
the metallic co-catalyst composition is present in a metal to rhodium molar ratio of at least 0.5:1 and up to 20:1.

15. The process according to claim 1, wherein:
the metallic co-catalyst composition comprises a metal selected from the group consisting of chromium and lanthanum and mixtures thereof, and optionally further includes a heteropoly acid (HPA).

* * * * *